United States Patent
Chu et al.

(10) Patent No.: US 8,955,517 B2
(45) Date of Patent: Feb. 17, 2015

(54) FOREHEAD SUPPORTS FOR FACIAL MASKS

(71) Applicant: ResMed Limited, Bella Vista, New South Wales (AU)

(72) Inventors: Vincent Chu, Middle Park (AU); Mark Bertinetti, Ermington (AU); Joshua A. Gudiksen, Mortdale (AU); Scott A. Howard, Frenchs Forest (AU); Susan R. Lynch, Bella Vista (AU); Eva Ng, Erskineville (AU); Phillip Thomas Stallard, Denistone East (AU); Murray William Lee, Quakers Hill (AU); Matthew Eves, Manley Vale (AU); Shiva Kumar Shanmuga Sundara, Toongabbie (AU)

(73) Assignee: ResMed Limited, Bella Vista (AU)

( * ) Notice: Subject to any disclaimer, the term of this patent is extended or adjusted under 35 U.S.C. 154(b) by 0 days.

(21) Appl. No.: 13/946,140

(22) Filed: Jul. 19, 2013

(65) Prior Publication Data

US 2013/0306076 A1 Nov. 21, 2013

Related U.S. Application Data

(63) Continuation of application No. 13/350,475, filed on Jan. 13, 2012, which is a continuation of application No. 12/308,462, filed as application No.
(Continued)

(51) Int. Cl.
*A62B 7/00* (2006.01)
*A62B 9/00* (2006.01)
(Continued)

(52) U.S. Cl.
CPC .......... *A61M 16/0683* (2013.01); *A61M 16/06* (2013.01); *A61M 16/0816* (2013.01); *A61M 16/0655* (2013.01)
USPC ............ 128/207.11; 128/205.23; 128/205.25; 128/845

(58) Field of Classification Search
USPC ............. 128/203.29, 204.11, 205.23, 205.25, 128/206.21, 206.24–206.25, 206.28, 128/207.11, 207.13, 207.17, 845
See application file for complete search history.

(56) References Cited

U.S. PATENT DOCUMENTS 2,140,164 A 12/1938 Moffatt
4,577,375 A 3/1986 Beaussant
(Continued)

FOREIGN PATENT DOCUMENTS

EP 1493462 1/2005
EP 1205205 6/2005
(Continued)

OTHER PUBLICATIONS

"Either". Collins English Dictionary. 2000. http://www.credoreference.com/entry/hcengdict/either (Sep. 14, 2013).*
(Continued)

*Primary Examiner* — Tan-Uyen (Jackie) T Ho
*Assistant Examiner* — Mark K Han
(74) *Attorney, Agent, or Firm* — Nixon & Vanderhye, P.C.

(57) ABSTRACT

A forehead support for a mask assembly includes a frame connector provided to a mask frame, a forehead cushion support movably mounted to the frame connector for generally linear movement between retracted and extended positions with respect to the frame connector, and an adjustment knob movably mounted to the frame connector and threadably engaged with the forehead cushion support such that turning movement of the adjustment knob causes the forehead cushion support to be moved between the retracted and extended positions. The adjustment knob includes a resilient prong having a ratchet bump. The ratchet bump is adapted to selectively engage a series of ridges provided to the frame connector to provide indexed incremental adjustment.

28 Claims, 46 Drawing Sheets

Related U.S. Application Data

PCT/AU2007/000837 on Jun. 15, 2007, now Pat. No. 8,327,850.

(60) Provisional application No. 60/858,694, filed on Nov. 14, 2006, provisional application No. 60/836,604, filed on Aug. 10, 2006, provisional application No. 60/814,056, filed on Jun. 16, 2006.

(51) Int. Cl.
*A62B 18/02* (2006.01)
*A62B 18/08* (2006.01)
*A61M 16/06* (2006.01)
*A61M 16/08* (2006.01)

(56) References Cited

U.S. PATENT DOCUMENTS

| | | | |
|---|---|---|---|
| 4,867,178 A * | 9/1989 | Smith | 128/858 |
| 4,944,210 A | 7/1990 | Flock et al. | |
| 6,119,693 A | 9/2000 | Kwok et al. | |
| 6,463,931 B1 | 10/2002 | Kwok et al. | |
| 6,532,961 B1 | 3/2003 | Kwok et al. | |
| 6,557,556 B2 | 5/2003 | Kwok et al. | |
| 6,615,834 B2 | 9/2003 | Gradon et al. | |
| 6,631,718 B1 * | 10/2003 | Lovell | 128/206.24 |
| 6,691,708 B2 | 2/2004 | Kwok et al. | |
| 6,789,541 B2 | 9/2004 | Olsen et al. | |
| 6,860,269 B2 * | 3/2005 | Kwok et al. | 128/207.11 |
| 7,059,326 B2 | 6/2006 | Heidmann et al. | |
| 7,069,932 B2 * | 7/2006 | Eaton et al. | 128/206.24 |
| 7,549,422 B2 | 6/2009 | Frerichs et al. | |
| 8,151,797 B2 | 4/2012 | Chang | |
| 8,176,919 B2 | 5/2012 | Chang | |
| 8,210,179 B2 * | 7/2012 | Eaton et al. | 128/206.24 |
| 8,245,711 B2 * | 8/2012 | Matula et al. | 128/207.11 |
| 8,256,421 B2 * | 9/2012 | Ho et al. | 128/207.11 |
| 2003/0062048 A1 | 4/2003 | Gradon et al. | |
| 2003/0089373 A1 | 5/2003 | Gradon et al. | |
| 2004/0112387 A1 | 6/2004 | Lang et al. | |
| 2004/0177850 A1 | 9/2004 | Gradon et al. | |
| 2004/0182398 A1 | 9/2004 | Sprinkle et al. | |
| 2005/0072428 A1 | 4/2005 | Ho et al. | |
| 2007/0044804 A1 | 3/2007 | Matula et al. | |
| 2007/0062537 A1 | 3/2007 | Chiesa et al. | |
| 2008/0210241 A1 | 9/2008 | Schulz et al. | |
| 2008/0276937 A1 | 11/2008 | Davidson et al. | |
| 2008/0314390 A1 | 12/2008 | Kwok et al. | |
| 2010/0000542 A1 | 1/2010 | Chu et al. | |
| 2010/0071700 A2 * | 3/2010 | Hitchcook et al. | 128/207.11 |
| 2011/0126838 A1 | 6/2011 | Alberici et al. | |
| 2012/0090617 A1 | 4/2012 | Matula et al. | |
| 2012/0111333 A1 | 5/2012 | Eifler et al. | |
| 2014/0000618 A1 * | 1/2014 | Belton | 128/205.25 |

FOREIGN PATENT DOCUMENTS

| | | |
|---|---|---|
| EP | 1632262 | 3/2006 |
| JP | 9-179061 | 7/1997 |
| JP | 2005-534383 | 11/2005 |
| JP | 2009-504320 | 2/2009 |
| WO | WO 00/78384 | 12/2000 |
| WO | 2004078228 | 9/2004 |
| WO | 2004078229 | 9/2004 |
| WO | 2004078230 | 9/2004 |
| WO | WO 2004/078231 | 9/2004 |
| WO | WO 2005/123166 | 12/2005 |
| WO | PCT/AU2006/000037 | 1/2006 |
| WO | 2006/050559 | 5/2006 |

OTHER PUBLICATIONS

English machine-translation of Abstract of EP 1493462 A2.*
English machine-translation of Description of EP 1493462 A2.*
English machine-translation of Claims of EP 1493462 A2.*
U.S. Appl. No. 60/643,113, filed Jan. 2005, Hitchcock et al.
New Zealand Further Examination Report for NZ Application No. 595423, dated Apr. 10, 2013, 2 pages.
New Zealand First Examination Report for NZ Application No. 608762, dated Apr. 10, 2013, 2 pages.
Notice of Allowance dated Aug. 13, 2012 for U.S. Appl. No. 12/308,462 including PTO-892 listing: 8,151,797; 8,176,919; 7,549,422; 2012/0111333; 2012/0090617; 2008/0314390; 2008/0276937; 2007/0044804; 2004/0112387; 2007/00062537; and 2011/0126838.
Office Action issued in related Japanese Appln. No. 2009-514595 (Dec. 20, 2011) w/ English translation.
International Search Report for PCT/AU2007/000837 (Jul. 16, 2007) (4 pages).
First Office Action issued in related Chinese Appln. 200780022443.9 (Feb. 25, 2011).
Fisher and Paykel, "FlexiFit™ 407 Nasal Mask, Patient Instructions for Use" Manual (front page), 1 page, USPTO to assume before Applicant's filing date*.
Fisher and Paykel, "FlexiFit™ 407 Nasal Mask", (manual image), 1 page, USPTO to assume before Applicant's filing date.
Fisher and Paykel, "FlexiFit™ 407 Nasal Mask", (image of a mask), 1 page, USPTO to assume before Applicant's filing date.
Fisher and Paykel, "FlexiFit™ 407 Nasal Mask", (image of a plate), 1 page, USPTO to assume before Applicant's filing date.
Fisher and Paykel, "FlexiFit™ 407 Nasal Mask", (image of support), 1 page, USPTO to assume before Applicant's filing date.
Non-final Official Action dated Jan. 28, 2014 in related U.S. Appl. No. 13/350,475 (24 pages).
"Knob". Collins English Dictionary. 2000. http://www.credoreference.com/entry/hcengdicUknob (Dec. 30, 2013).
"Either". Collins English Dictionary. 2000. http://www.credoreference.com/entry/hcengdict/either (Dec. 30, 2013).
"Cavity". Collins English Dictionary. 2000. http://www.credoreference.com/entry/hcengdict/cavity (Dec. 30, 2013).
European Communication with extended European Search Report in European Application No. 12165173.1 dated Feb. 26, 2014 (5 pages).
Notice of Allowance issued on Sep. 2, 2014 in related U.S. Appl. No. 13/350,475, filed Jan. 13, 2012, 15 pages.
Notification of First Office Action issued in corresponding Chinese Application No. 201110369393.X with English translation dated Jan. 13, 2014, 17 pages.
Chinese Notification of Second Office Action w/ English Translation issued Application No. 201110369393.X, dated Nov. 15, 2014, (11 pages).

* cited by examiner

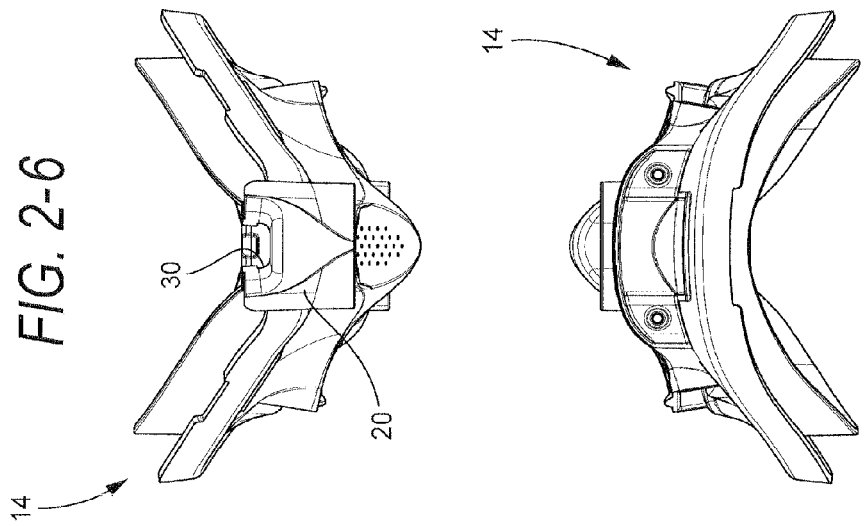
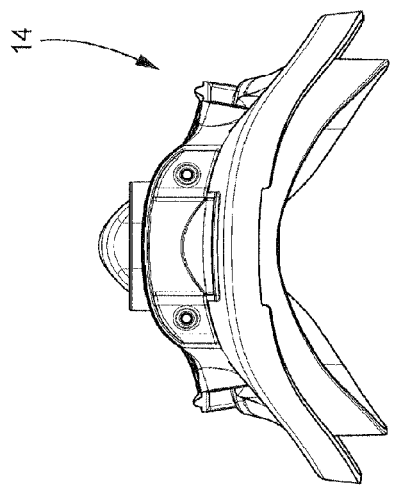
FIG. 2-6
FIG. 2-7
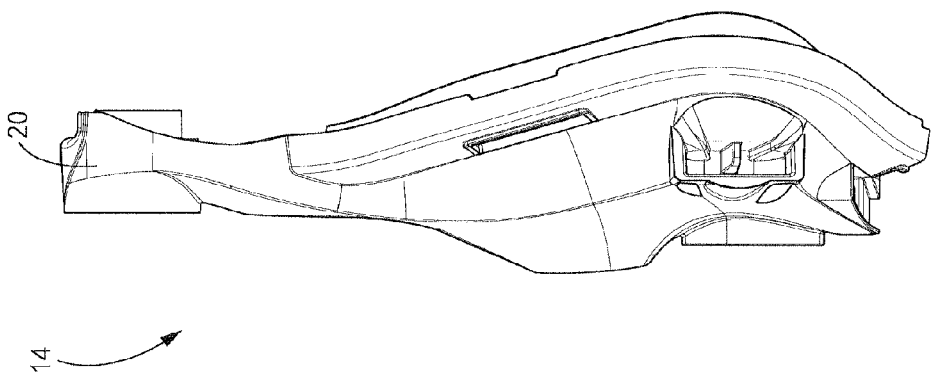
FIG. 2-5

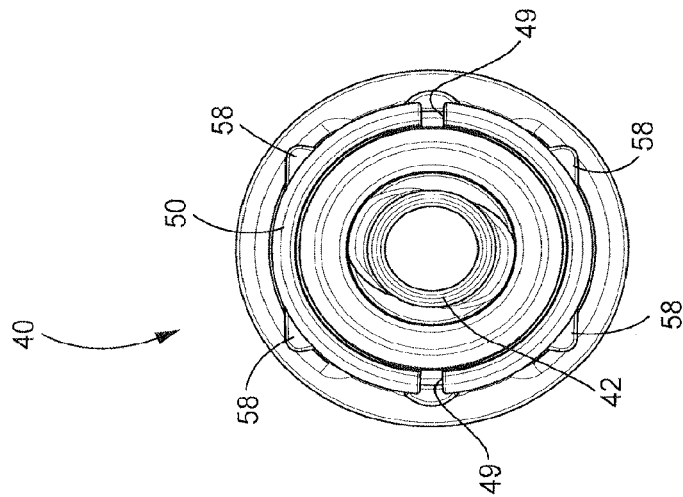
FIG. 4-6
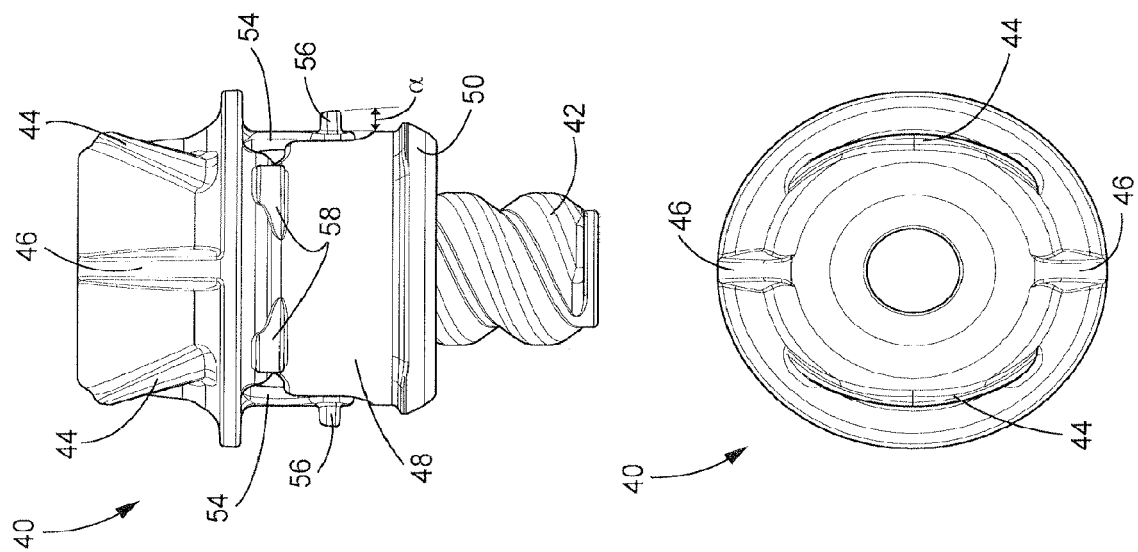
FIG. 4-7
FIG. 4-5

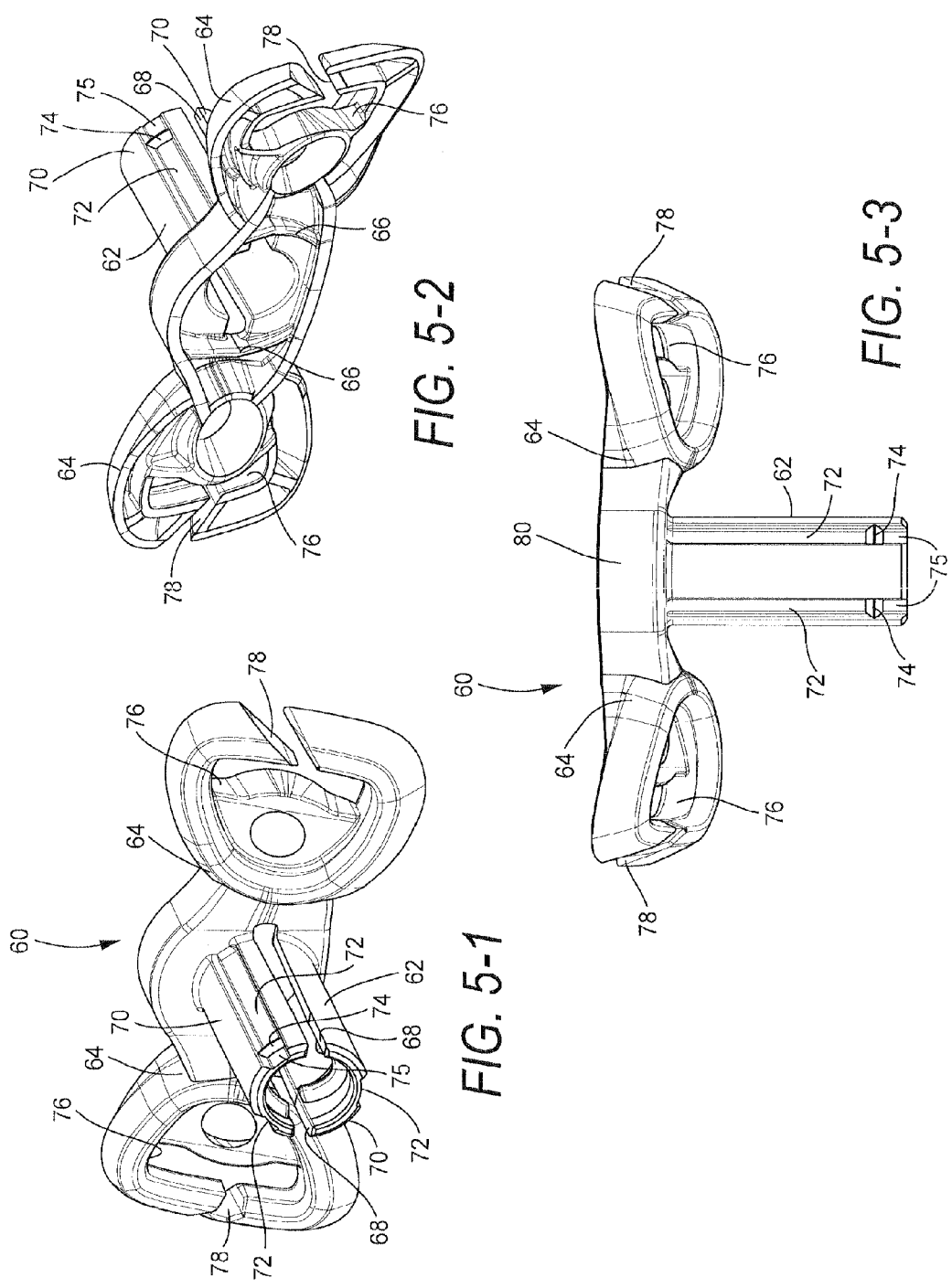

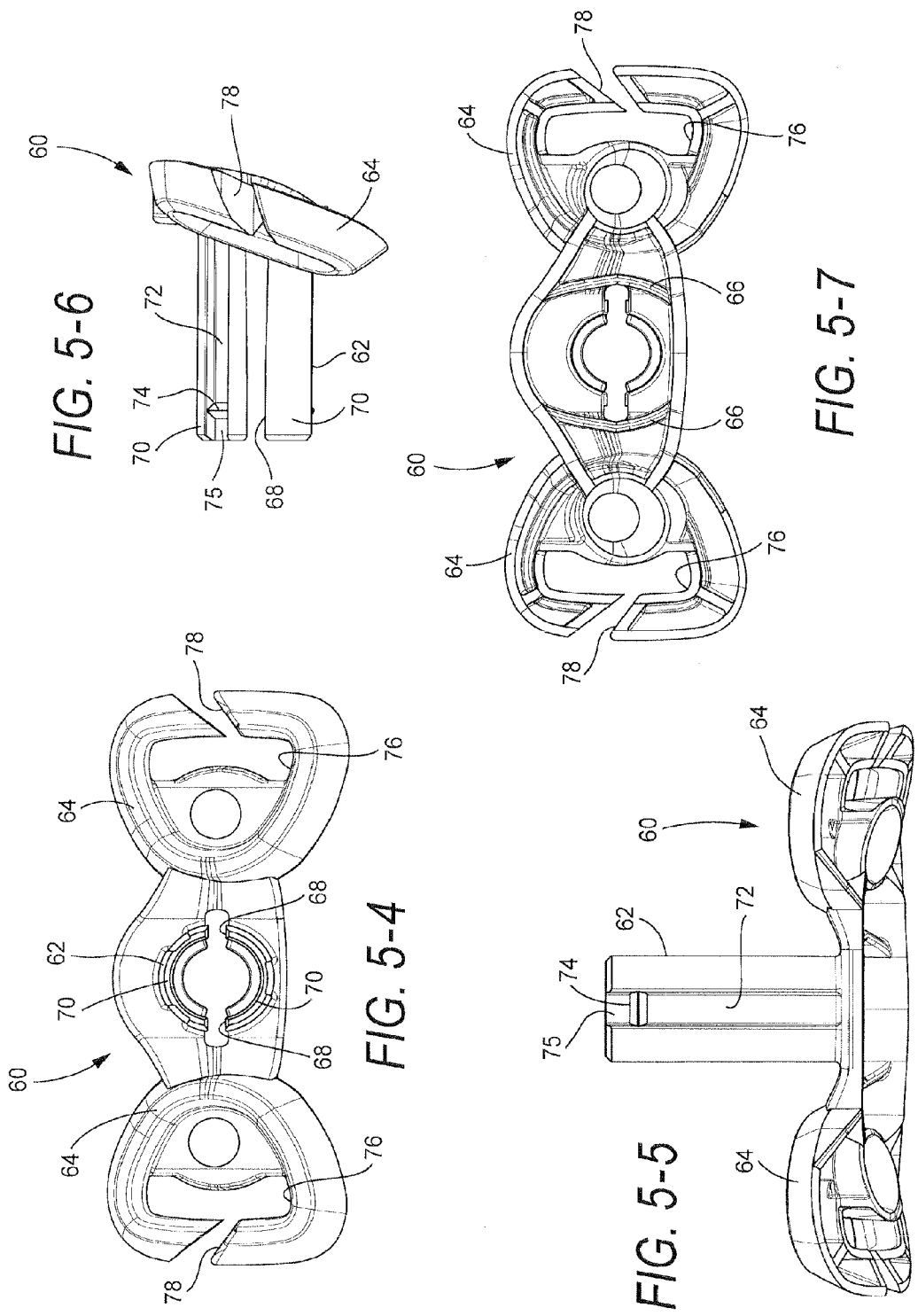

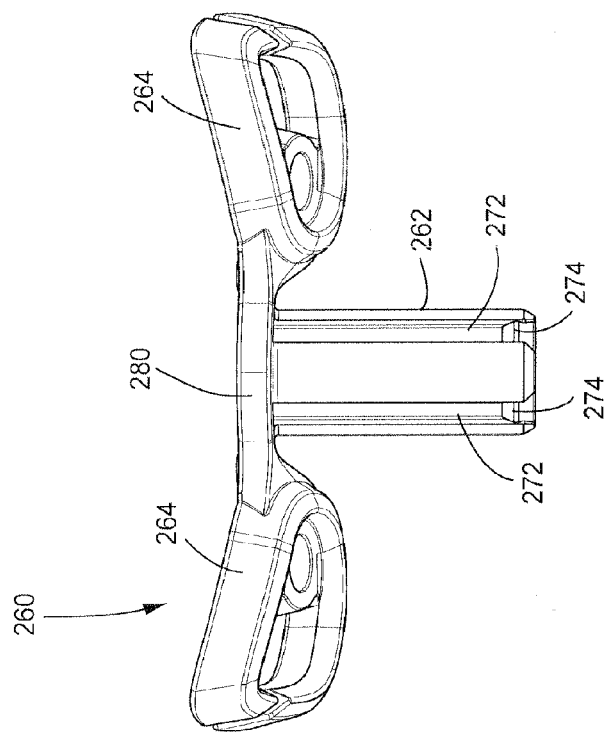
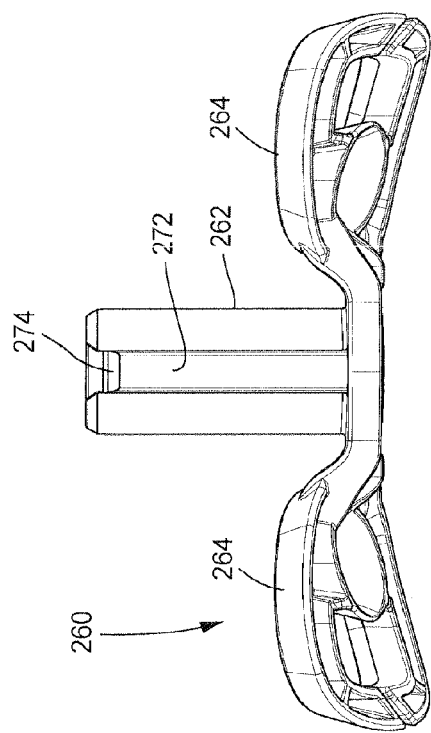

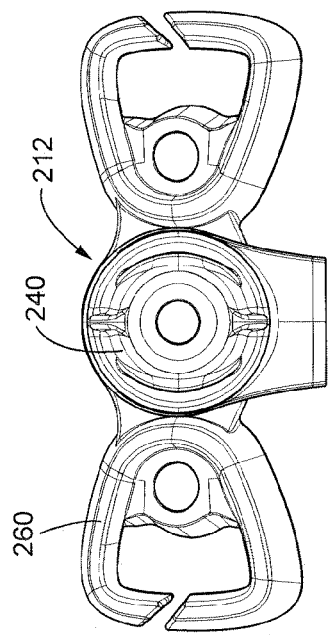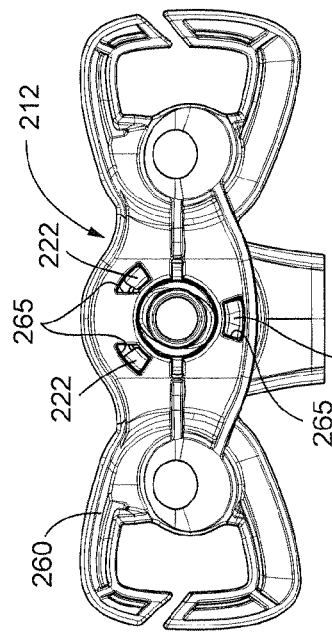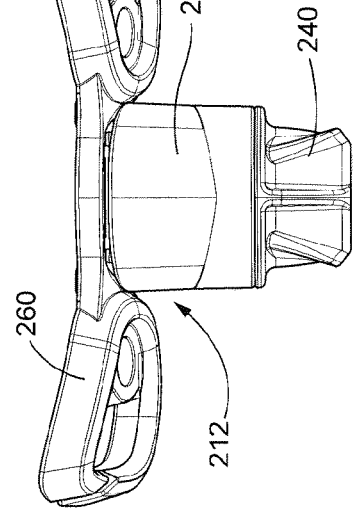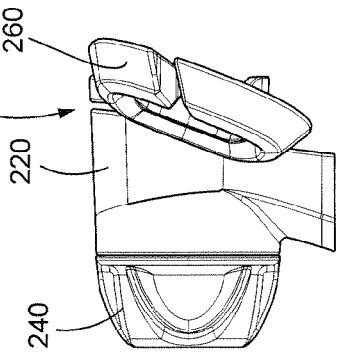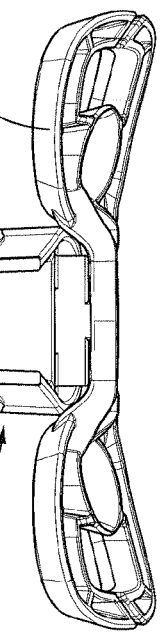

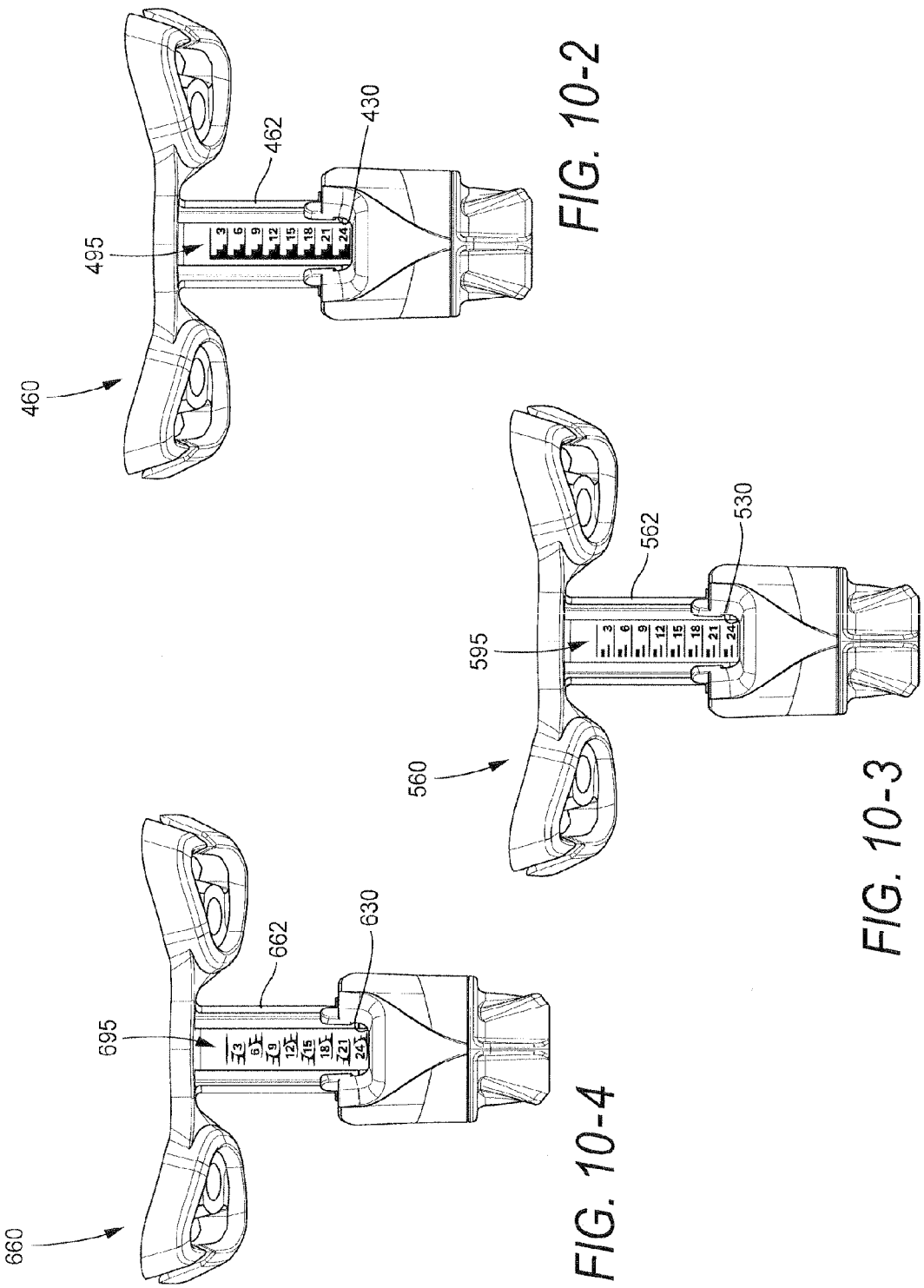

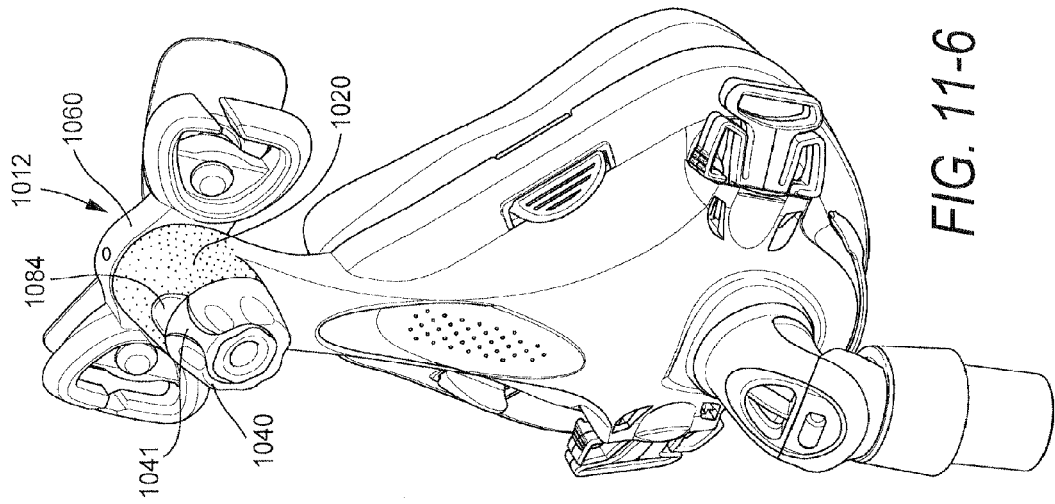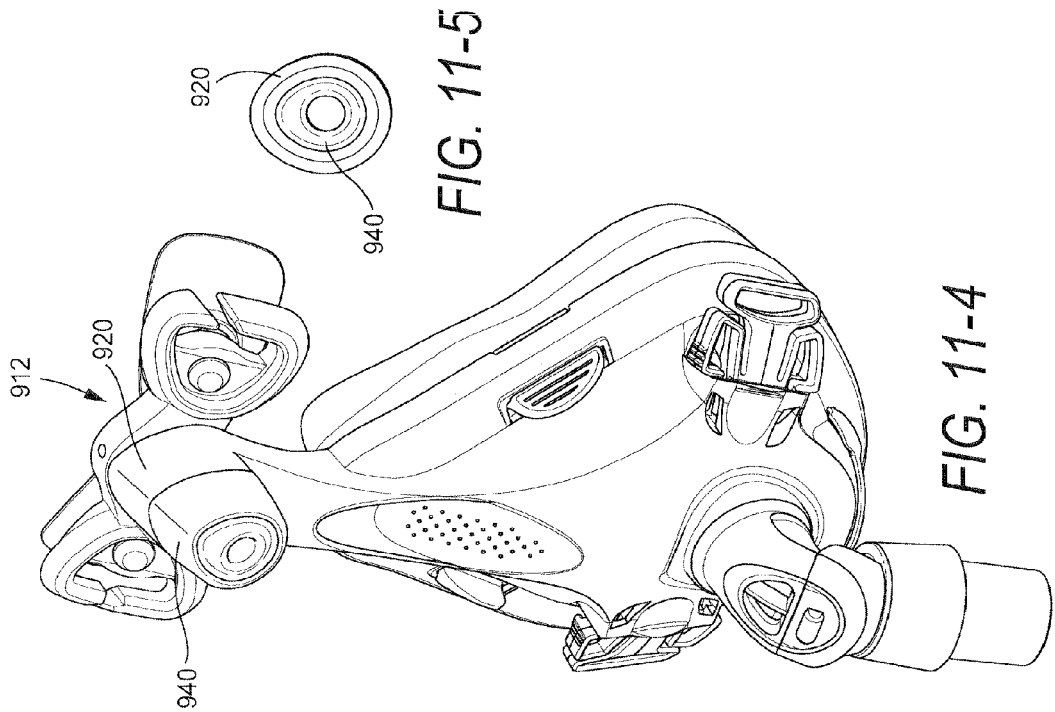

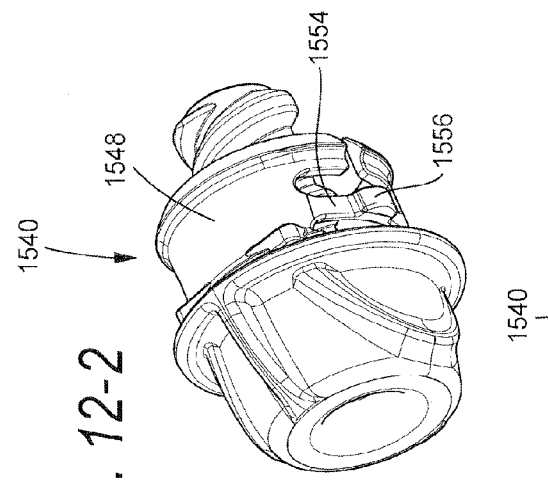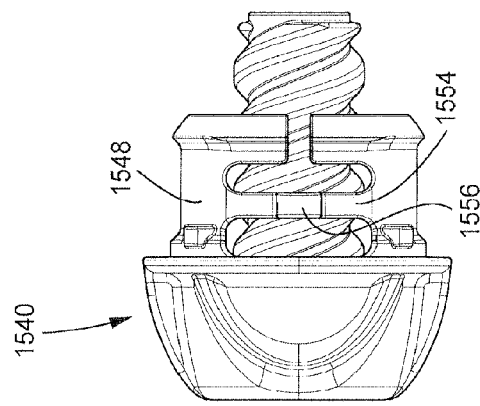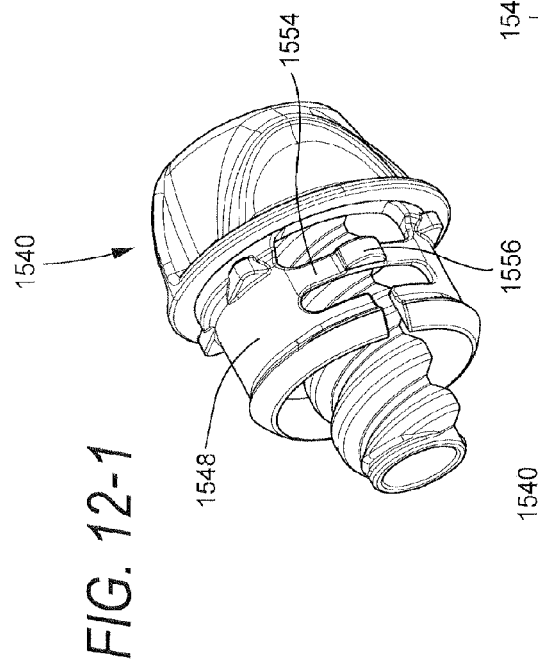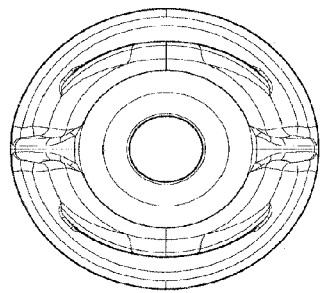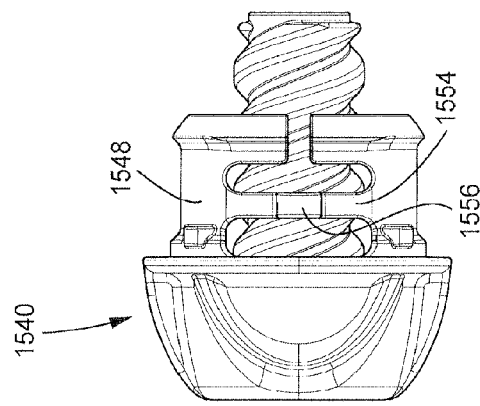

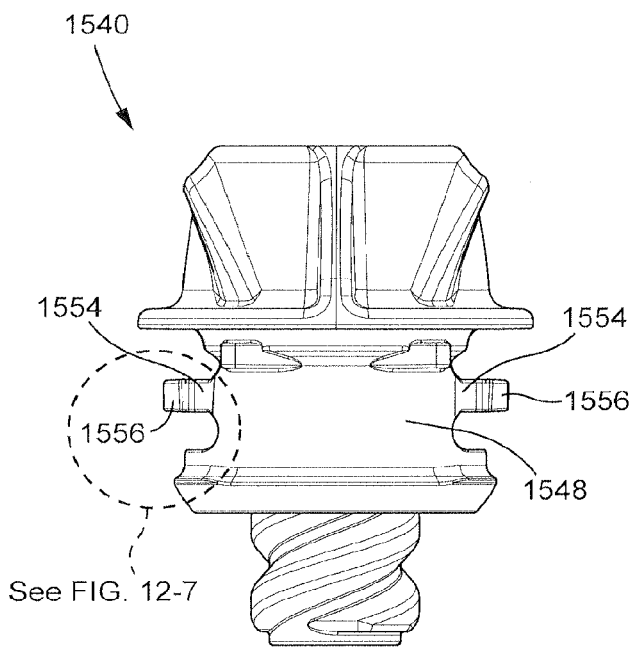
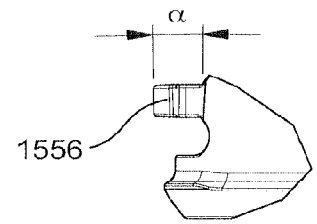
FIG. 12-6    FIG. 12-7
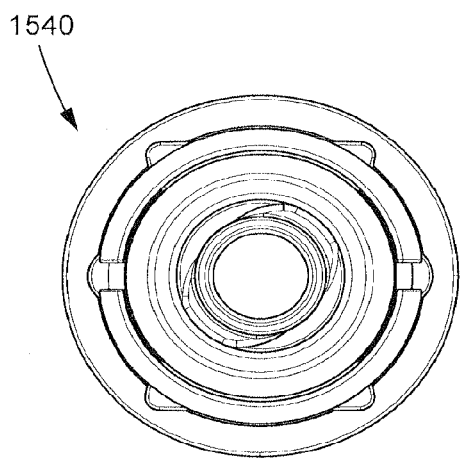
FIG. 12-8
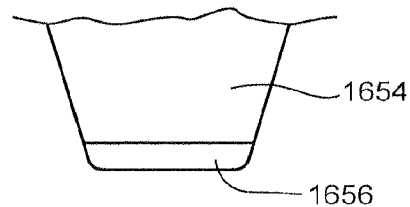
FIG. 13

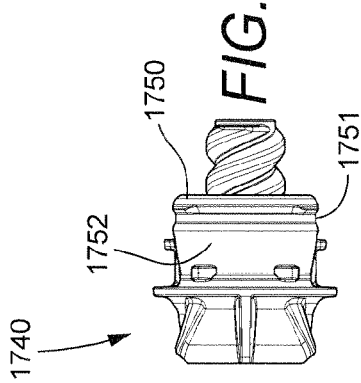
FIG. 14-3   FIG. 14-4
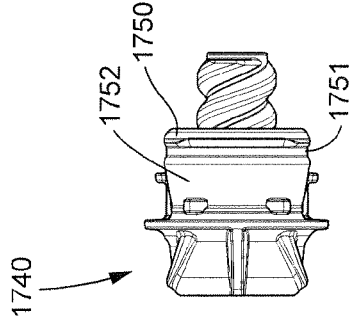
FIG. 14-5   FIG. 14-6
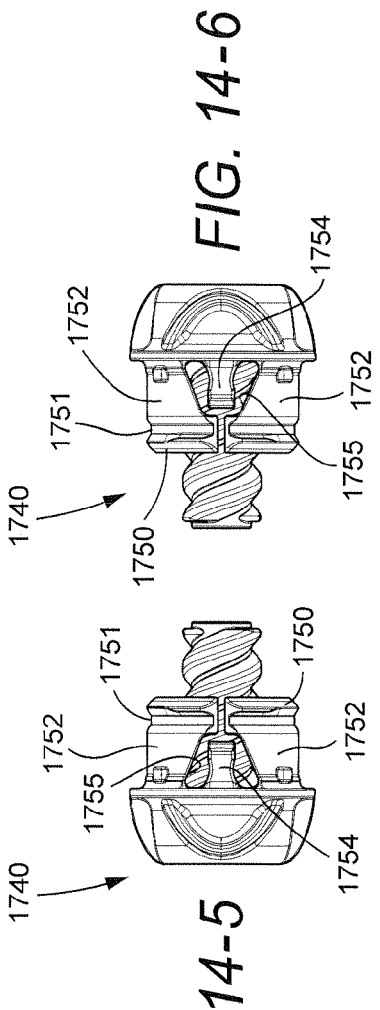
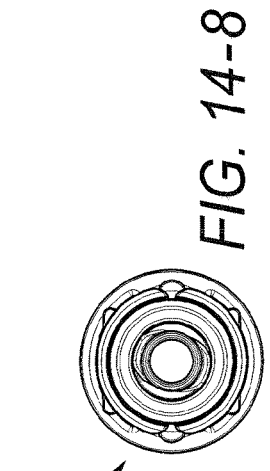
FIG. 14-7
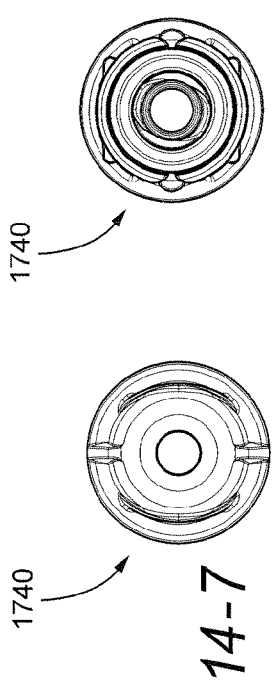
FIG. 14-8
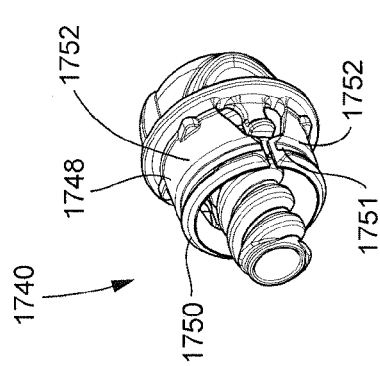
FIG. 14-1   FIG. 14-2
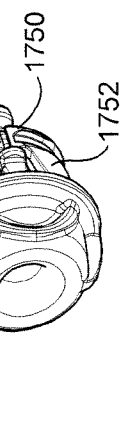

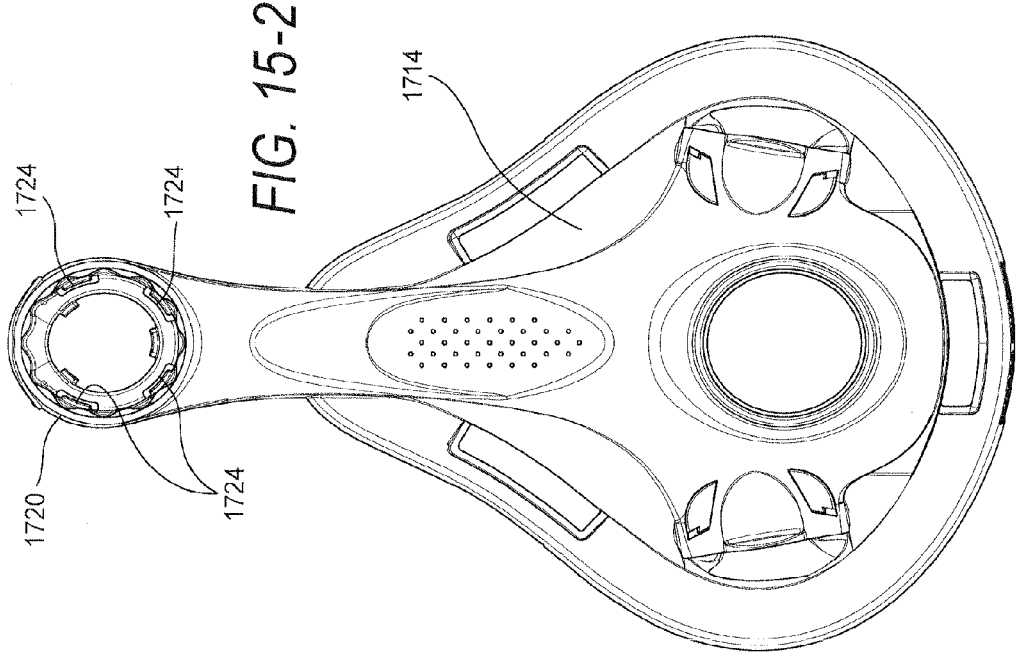
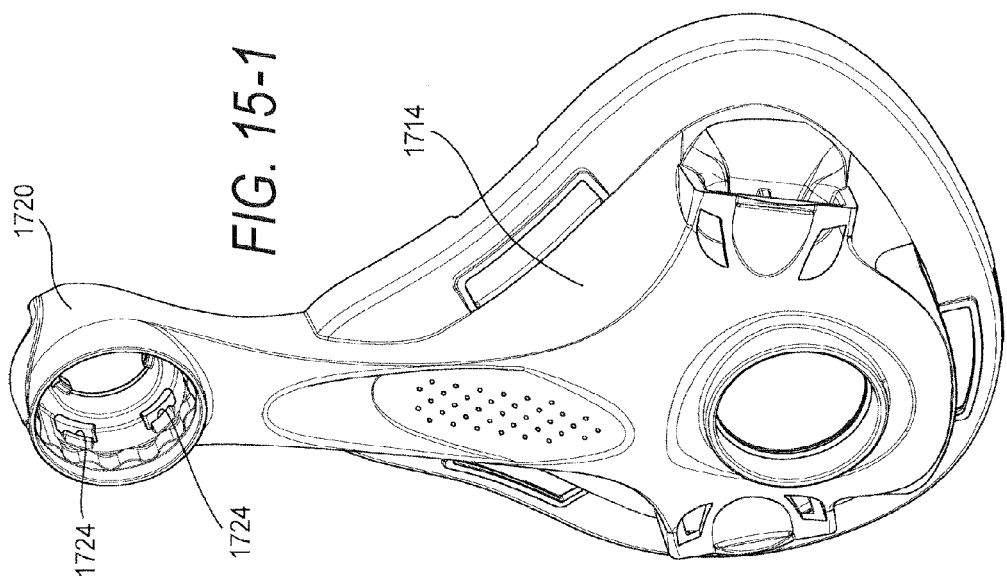

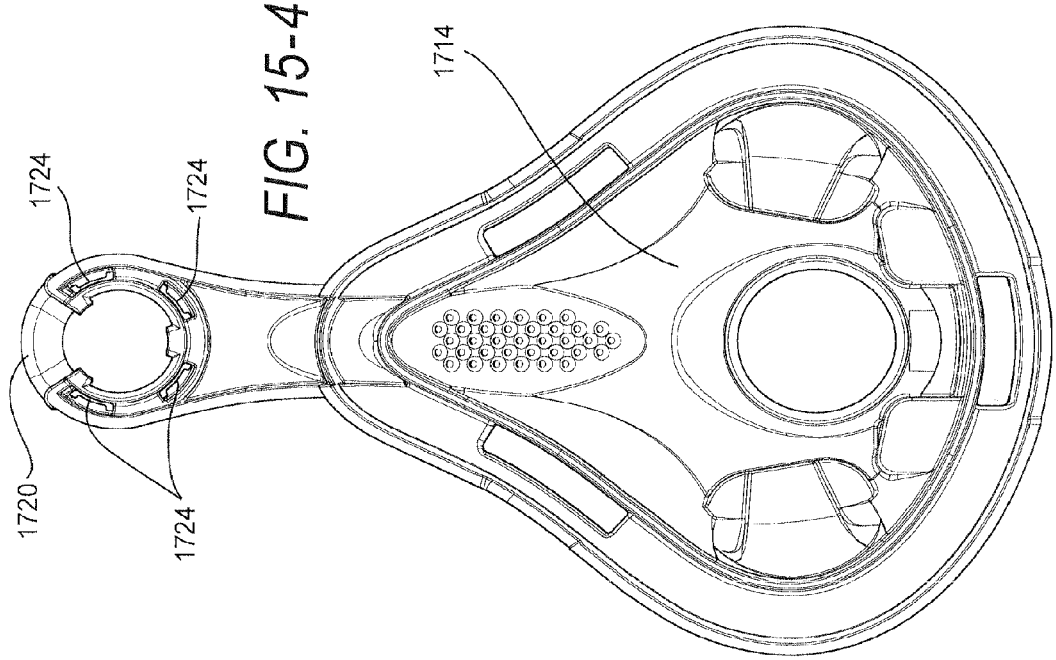
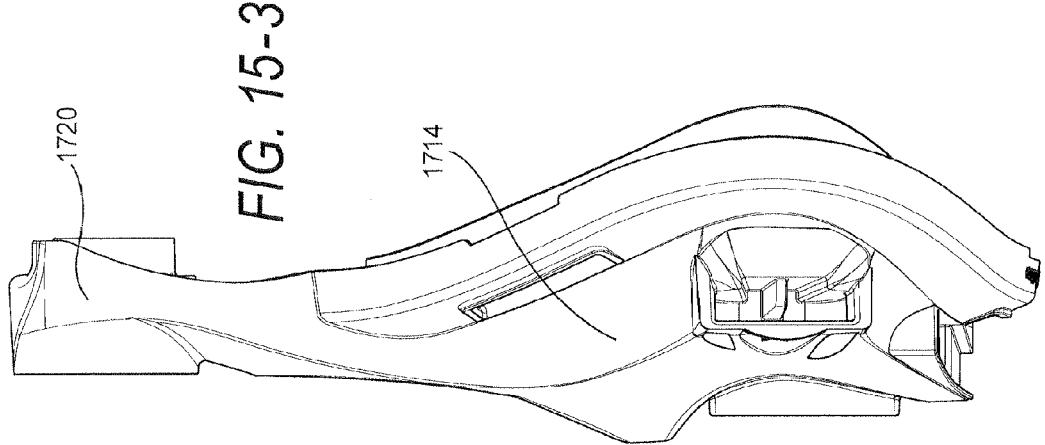

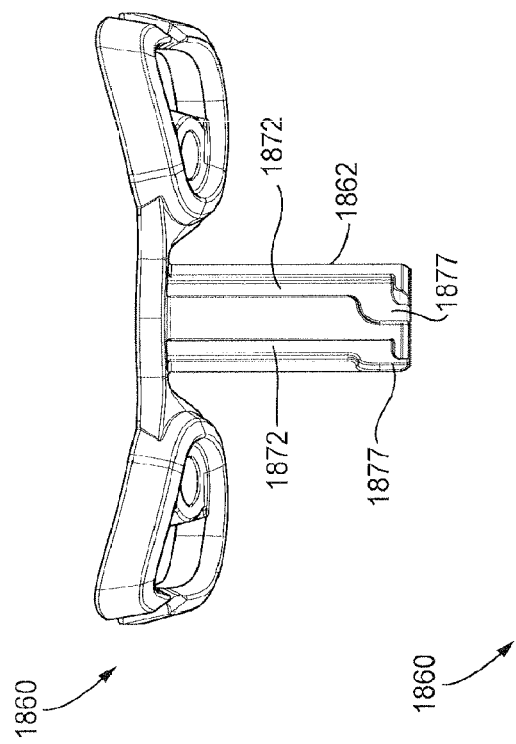
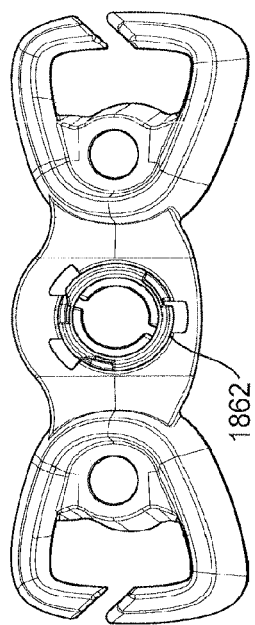
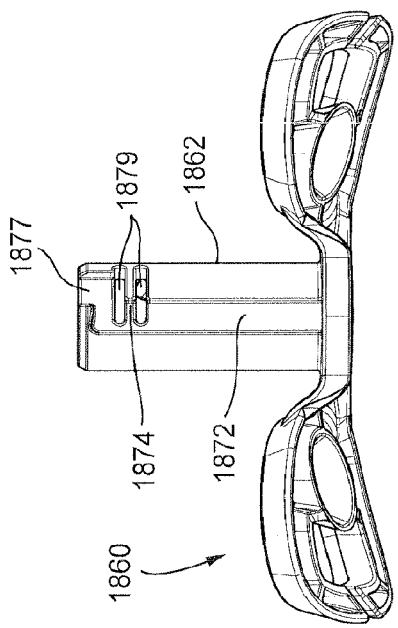
FIG. 16-1
FIG. 16-2
FIG. 16-3

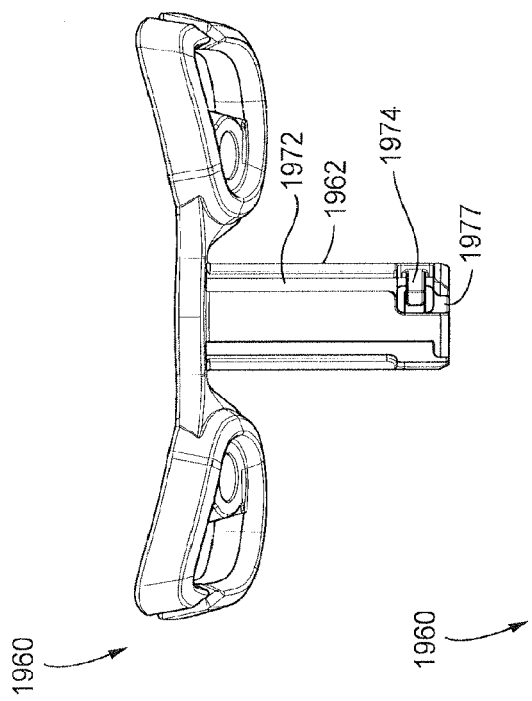
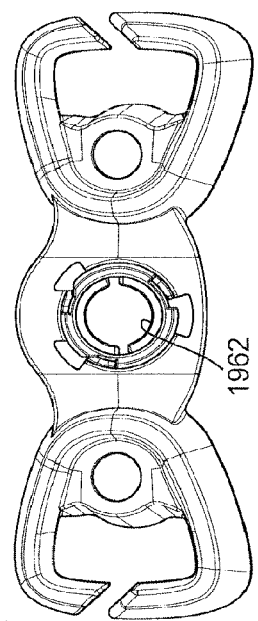
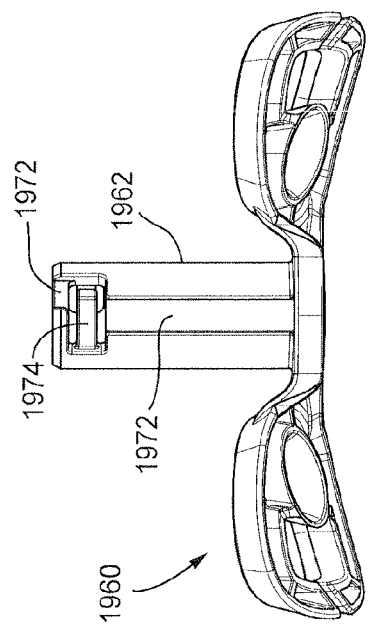
FIG. 17-1  FIG. 17-2  FIG. 17-3

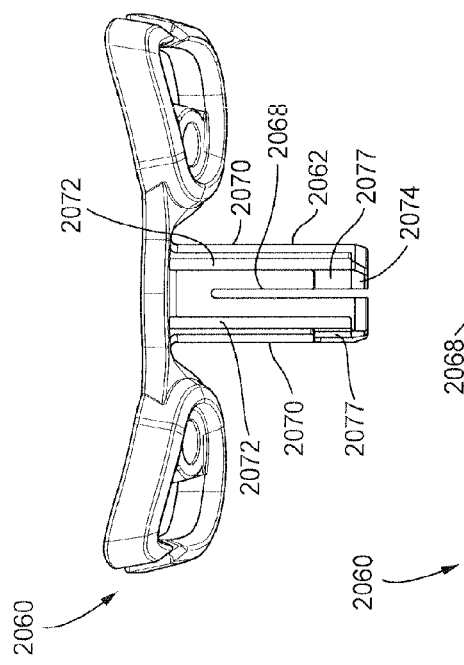
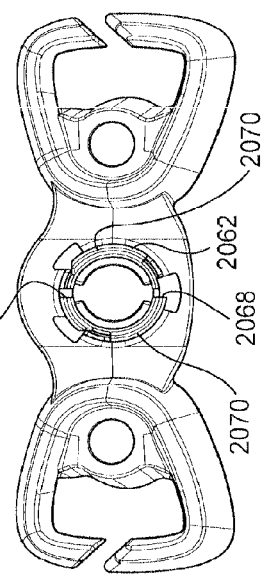
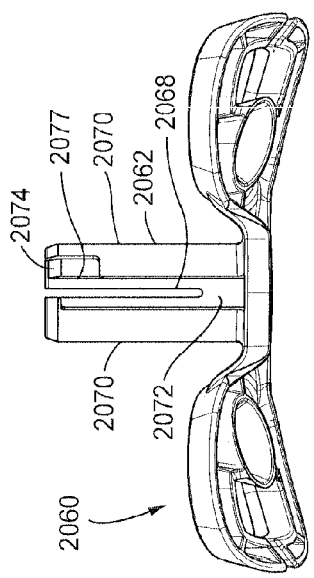
FIG. 18-1
FIG. 18-2
FIG. 18-3

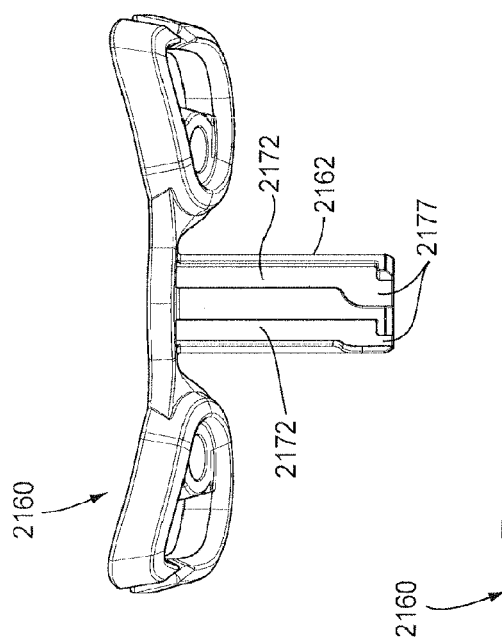
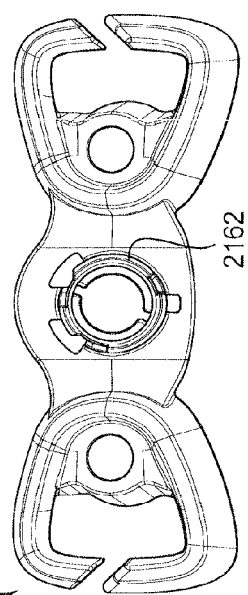
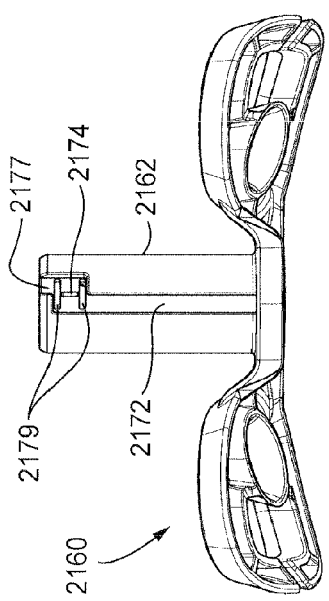
FIG. 19-1
FIG. 19-2
FIG. 19-3

FOREHEAD SUPPORTS FOR FACIAL MASKS

CROSS-REFERENCE TO APPLICATIONS

This application is a continuation of U.S. application Ser. No. 13/350,475, filed Jan. 13, 2012, which is a continuation of U.S. application Ser. No. 12/308,462, filed Dec. 16, 2008, now U.S. Pat. No. 8,327,850, which is the U.S. national phase of International Application Serial No. PCT/AU2007/000837, filed Jun. 15, 2007, which designated the U.S. and claims the benefit of U.S. Provisional Patent Application Ser. Nos. 60/814,056, filed Jun. 16, 2006, 60/836,604, filed Aug. 10, 2006, and 60/858,694, filed Nov. 14, 2006, each of which is incorporated herein by reference in its entirety.

Also, PCT Application No. PCT/AU2006/000037, filed Jan. 12, 2006, is incorporated herein by reference in its entirety.

FIELD OF THE INVENTION

The present invention relates generally to the field of forehead supports for facial masks used to supply breathable gas to a wearer's airways.

BACKGROUND OF THE INVENTION

Facial masks are well known for use in continuous positive airway pressure (CPAP) treatment of various respiratory ailments and sleep disordered breathing (SDB), such as, for example, obstructive sleep apnea (OSA) and/or other ventilatory assistance treatments such as noninvasive positive pressure ventilation (NPPV). See, for example, U.S. Pat. No. 4,944,210, the entire content of which is expressly incorporated hereinto by reference.

Apparatus for the treatment of SDB generally involves a blower which delivers a supply of air at positive pressure to a patient interface via a conduit. The patient interface may take several forms, such as a nasal mask assembly and a nasal and mouth mask assembly (i.e., a full face mask). Patients typically wear a mask assembly while sleeping to receive the NPPV therapy.

Mask assemblies typically include a rigid shell or frame and a soft face-contacting cushion. The cushion cushions the rigid frame from the patient's face, and provides a seal with the patient's face. The frame and cushion define a cavity which receives the nose or nose and mouth. The frame and cushion are held in position on the patient's face by a headgear assembly. The headgear assembly typically comprises an arrangement of straps which pass along both sides of the patient's face to the back or crown of the patient's head.

One problem that arises with existing masks used for CPAP treatments is that tightening of the mask straps results in compression of the mask against the wearer's face which may therefore apply undue force against certain of the wearer's facial features, such as the wearer's nose. A poorly fitting mask can leak when pressurized which encourages a patient to tighten the headgear straps excessively which, in turn leads to discomfort, marks on the face and in some cases facial sores.

Thus, conventional masks have been provided with a forehead support, which provides a support and stability mechanism between the mask and the forehead. The forehead support prevents both the mask from pushing too strongly against the wearer's facial region as well as minimizing movement of the mask with the addition of a contact point between the mask and the wearer's head thereby reducing uncomfortable pressure points. Furthermore, in facial masks having a gusseted facial cushion such as described in co-pending U.S. Provisional Patent Application Ser. No. 60/643,113, filed Jan. 12, 2005, the entire content of which is expressly incorporated hereinto by reference, a forehead support may be employed to control the amount of gusset opening and/or closing thereby assisting in the applied force to the wearer's face, for example, the patient's nasal region.

Typically, a mask forehead support is adjustable so that a standard mask may be capable of adjustment suitable for a number of patients with different anthropometric features. Conventional masks having adjustable forehead supports are evidenced by U.S. Pat. Nos. 6,119,693; 6,463,931; 6,557,556; and 6,691,708, the entire content of each such prior-issued patent being incorporated expressly hereinto by reference. To facilitate adjustability, conventional forehead supports may also be capable of displacement relative to the mask as shown, for example, in U.S. Pat. No. 6,532,961 (the entire content of which is expressly incorporated hereinto by reference), so as to provide a means by which the relative angle between the mask and the forehead support can be varied to accommodate the facial features of a particular wearer.

A problem with conventional forehead supports for masks, however, is that the range of adjustment is relatively limited which therefore does not in fact provide a universal fit for a relatively large number of wearers. That is, due to the anthropometric features of a particular user's head, the adjustability of conventional forehead supports may not be sufficient to allow for a comfortable fit. Thus, while the forehead supports described above perform in a satisfactory manner, improvements to forehead supports for masks are needed.

SUMMARY OF THE INVENTION

In one embodiment, a mask forehead support provides for greater universality of fit as compared to conventional forehead support structures. More specifically, according to embodiments of the present invention, forehead supports are provided which are capable of a more useful and beneficial range of adjustment as compared to conventional forehead support structures thereby allowing the forehead supports of the present invention to more universally fit a much larger number of patients.

One aspect of the present invention relates to a forehead support for a mask assembly including a frame connector provided to a mask frame, a forehead cushion support movably mounted to the frame connector for generally linear movement between retracted and extended positions with respect to the frame connector, and an adjustment knob movably mounted to the frame connector and threadably engaged with the forehead cushion support such that turning movement of the adjustment knob causes the forehead cushion support to be moved between the retracted and extended positions. The adjustment knob includes a resilient prong having a ratchet bump. The ratchet bump is adapted to selectively engage a series of ridges provided to the frame connector to provide indexed incremental adjustment.

Another aspect of the present invention relates to a forehead support for a mask assembly including a frame connector provided to a mask frame, a forehead cushion support movably mounted to the frame connector for generally linear movement between retracted and extended positions with respect to the frame connector, and an adjustment knob movably mounted to the frame connector. The knob includes a threaded shaft that is threadably engaged with an internally threaded tube provided to the forehead cushion support such that turning movement of the adjustment knob causes the forehead cushion support to be moved between the retracted and extended positions. The frame connector has a cut-out that allows an upper portion of the tube to be visible.

Another aspect of the present invention relates to a forehead support for a mask assembly. The forehead support includes a frame connector provided to a mask frame, a forehead cushion support movably mounted to the frame connector for generally linear movement between retracted and extended positions with respect to the frame connector, and an adjustment knob movably mounted to the frame connector. The knob includes a threaded shaft that is threadably engaged with an internally threaded tube provided to the forehead cushion support such that turning movement of the adjustment knob causes the forehead cushion support to be moved between the retracted and extended positions. Position markings are provided to the frame connector and/or the adjustment knob to indicate a position of the forehead cushion support.

It will of course be understood that, while the present invention will be described in connection with a full facial mask, those in this art will recognize that such a description represents one preferred embodiment and is thus non-limiting. Thus, the structural and/or functional features of the present invention may, for example, also be usefully employed in nasal masks or nasal prongs, nozzles, nare seals, and/or cannulae.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIGS. 2-1 to 2-7 show various views of a frame of the mask assembly shown in FIGS. 1-1 to 1-10;

FIGS. 3-1 to 3-6 show various views of a frame connector of the forehead support shown in FIGS. 1-1 to 1-10;

FIGS. 4-1 to 4-7 show various views of an adjustment knob of the forehead support shown in FIGS. 1-1 to 1-10;

FIGS. 5-1 to 5-7 show various views of a forehead cushion support of the forehead support shown in FIGS. 1-1 to 1-10;

FIGS. 6-1 to 6-7 show various views of a frame connector according to another embodiment of the present invention;

FIGS. 7-1 to 7-8 show various views of an adjustment knob according to another embodiment of the present invention;

FIGS. 8-1 to 8-7 show various views of a forehead cushion support according to another embodiment of the present invention;

FIGS. 9-1 to 9-8 show various assembly views of the frame connector, adjustment knob, and forehead cushion support shown in FIGS. 6-1 to 6-7, 7-1 to 7-8, and 8-1 to 8-7;

FIGS. 10-1 to 10-5 show position markings on a forehead cushion support according to embodiments of the present invention;

FIGS. 11-1 to 11-15 show position markings provided to the frame connector and/or the adjustment knob according to embodiments of the present invention;

FIGS. 12-1 to 12-8 show various views of an adjustment knob according to another embodiment of the present invention;

FIG. 13 is a schematic view of a resilient prong for an adjustment knob according to another embodiment of the present invention;

FIGS. 14-1 to 14-8 show various views of an adjustment knob according to another embodiment of the present invention;

FIGS. 15-1 to 15-4 show various views of a frame according to another embodiment of the present invention;

FIGS. 16-1 to 16-7 show various views of a forehead cushion support according to another embodiment of the present invention;

FIGS. 17-1 to 17-7 show various views of a forehead cushion support according to another embodiment of the present invention;

FIGS. 18-1 to 18-7 show various views of a forehead cushion support according to another embodiment of the present invention; and FIGS. 19-1 to 19-7 show various views of a forehead cushion support according to another embodiment of the present invention.

DETAILED DESCRIPTION OF ILLUSTRATED EMBODIMENTS

Figure 1:
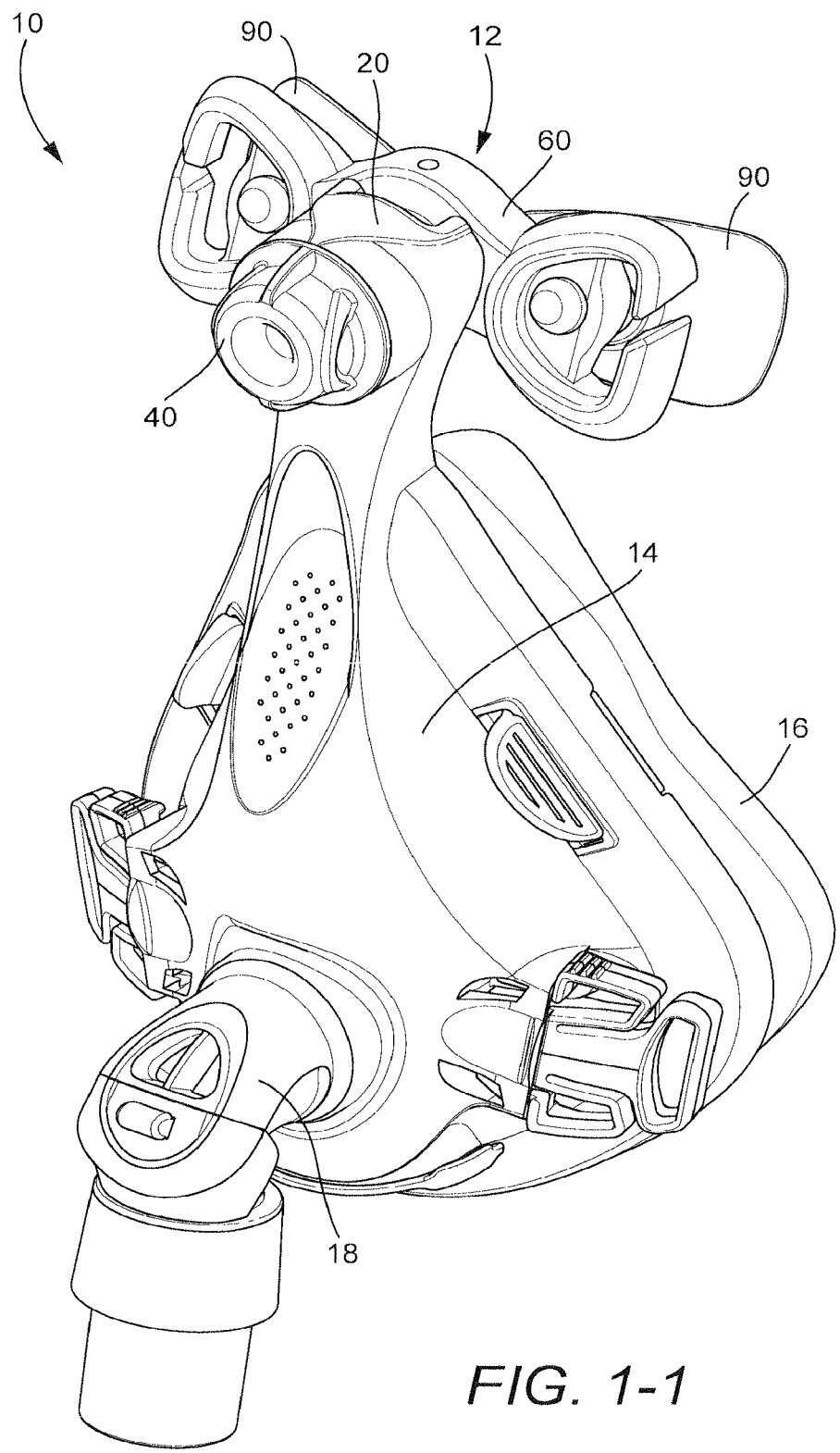
FIGS. 1-1 to 1-10 show various views of a full facial mask assembly including a forehead support according to an embodiment of the present invention.

The following includes descriptions of several illustrated embodiments of the present invention, which may share common characteristics and features. It is to be understood that one or more features of any one embodiment may be combinable with one or more features of the other embodiments. In addition, each single feature or combination of features in any of the embodiments may constitute an additional embodiment.

Each illustrated embodiment includes features that may be used with the embodiments and/or components described in PCT Application No. PCT/AU2006/000037, as would be apparent to those of ordinary skill in the art. PCT/AU2006/000037 is incorporated herein by reference in its entirety.

1. First Illustrated Embodiment of Forehead Support

FIGS. 1-1 to 1-10 illustrate a full facial mask assembly ("FMA") 10 including a forehead support 12 according to an embodiment of the present invention. As illustrated, the mask assembly 10 includes a frame 14 (see FIGS. 2-1 to 2-7), a cushion 16 provided to the frame 14 and adapted to form a seal with the patient's face, an elbow assembly 18 provided to the frame 14 and adapted to be connected to an air delivery tube that delivers breathable gas to the patient, and a forehead support 12 (see FIGS. 2-1 to 5-7) to provide a support and stability mechanism between the mask assembly 10 and the patient's forehead. A headgear assembly (not shown) may be removably attached to the frame 14 and the forehead support 12 to maintain the mask assembly 10 in a desired adjusted position on the patient's face.

Further details and embodiments of mask assemblies and forehead supports are disclosed in PCT Application No. PCT/AU2006/000037, the entirety incorporated herein by reference. While the forehead support 12 is described as being implemented into a mask assembly of the type described above, it may be implemented into other mask systems, e.g., full-face mask, mouth mask, or a nasal mask.

In this embodiment, the forehead support 12 uses a screw-type actuator to move the forehead support 12 along a generally linear path. The main components of the forehead support 12 are a frame connector 20 (also referred to as a support or a receiver) provided to the mask frame 14 (see FIGS. 2-1 to 3-6), an adjustment knob 40 (also referred to as a dial) including a threaded shaft 42 (see FIGS. 4-1 to 4-7), and a forehead cushion support 60 (also referred to as a t-bar) including an internally threaded tube 62 (see FIGS. 5-1 to 5-7). The forehead cushion support 60 carries forehead cushions 90 that are adapted to engage the patient's forehead in use (see FIGS. 1-1 to 1-10). Further details and embodiments of forehead cushions are disclosed in PCT Application No. PCT/AU2006/000037, the entirety incorporated herein by reference.

In an embodiment, the components may be assembled by first inserting the internally threaded tube 62 of the forehead cushion support 60 into the frame connector 20, and then assembling the adjustment knob 40 to the frame connector 20 and the forehead cushion support 60. However, other assembly sequences are possible, e.g., knob first and then forehead cushion support such as the arrangements shown in FIGS. 16-1 to 19-7 for example. Further details of assembly are described below.

When the adjustment knob 40 is rotated, the internally threaded tube 62 of the forehead cushion support 60 extends or retracts from the threaded shaft 42 of the adjustment knob 40, which causes adjustable movement of the forehead cushions 90.

In an embodiment, the components may be disassembled by rotating the adjustment knob 40 until it releases from the internally threaded tube 62 of the forehead cushion support 60, and then pulling off, e.g., snapping off, the adjustment knob 40 from the frame connector 20. That is, the knob 40 is over-rotated or over-torqued at the end of travel along the tube 62 to release the knob 40 from the tube 62 and the frame connector 20. Next, the forehead cushion support 60 may be pulled out of the frame connector 20.

1.1 Forehead Cushion Support

Figures 1, 2:
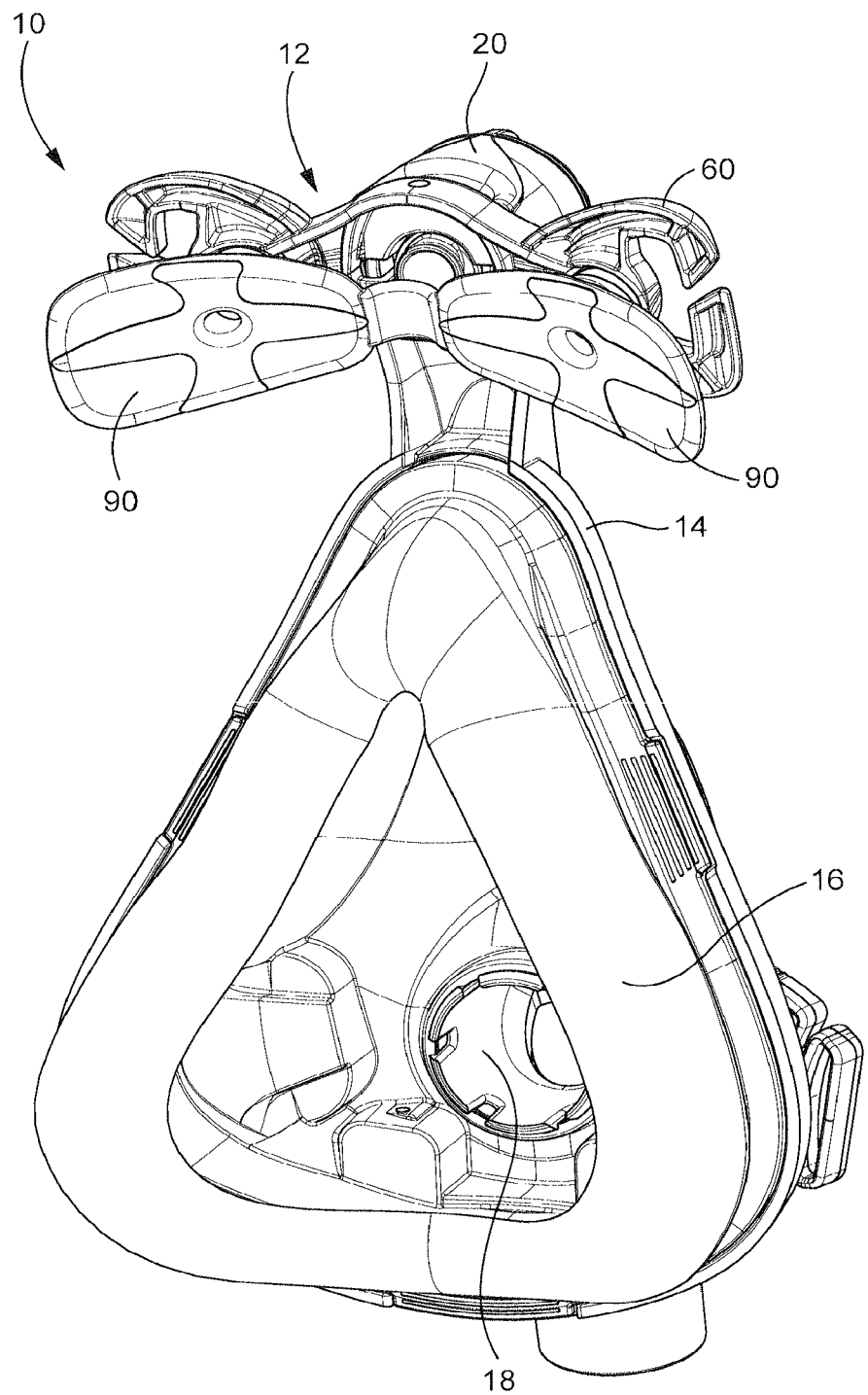
Figures 1, 2, 3:
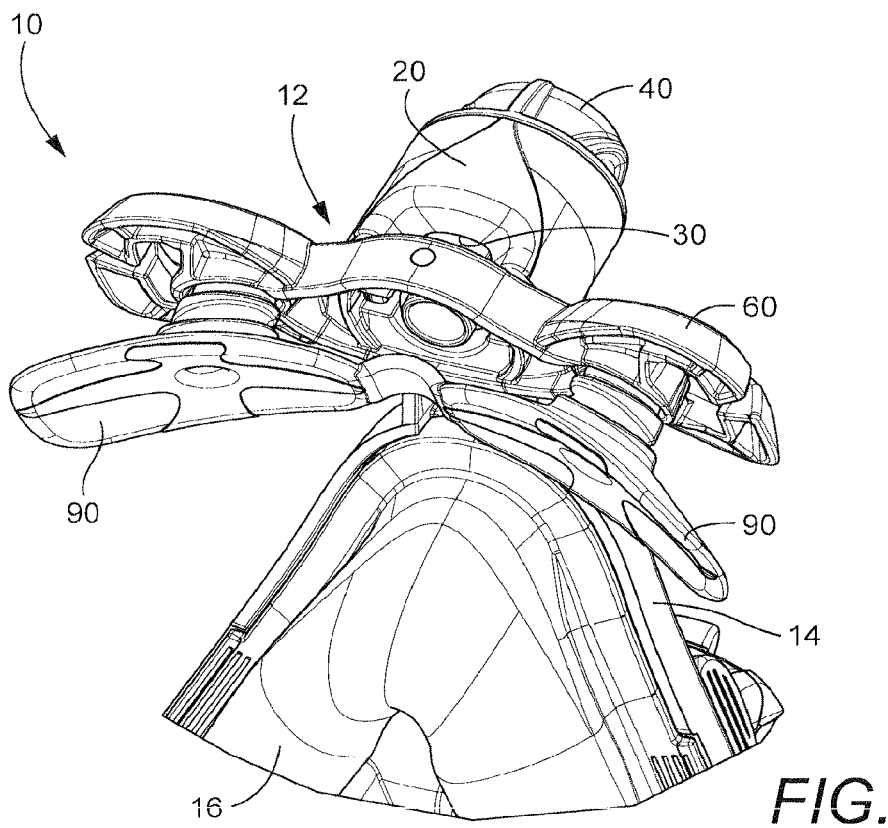
Figures 1, 2, 3, 4:
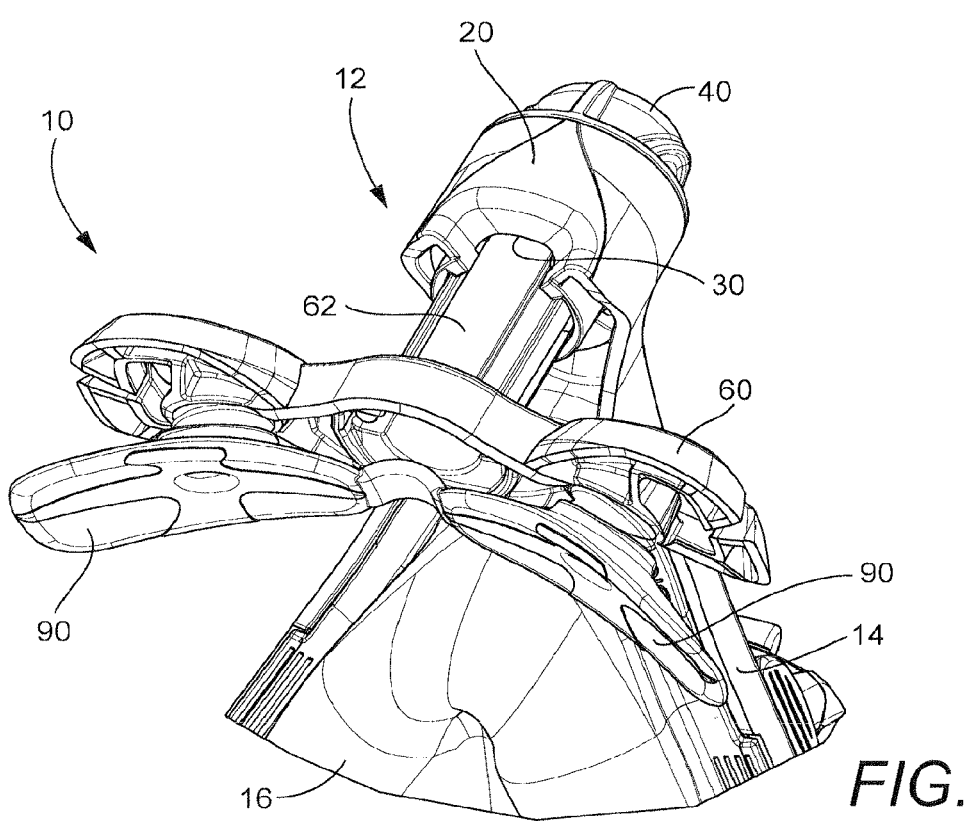
Figures 1, 2, 3, 4, 5:
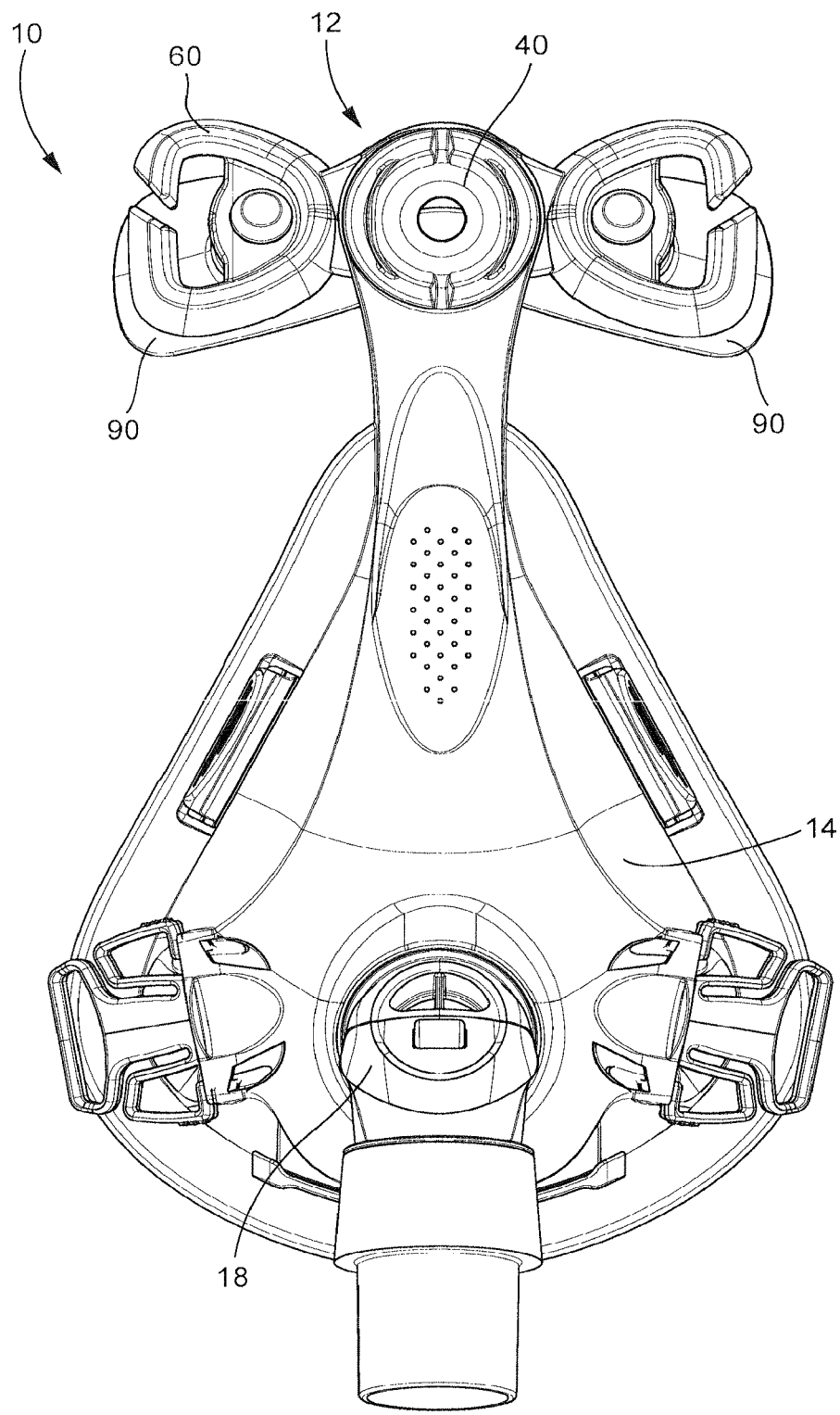
Figures 1, 2, 3, 4, 5, 6:
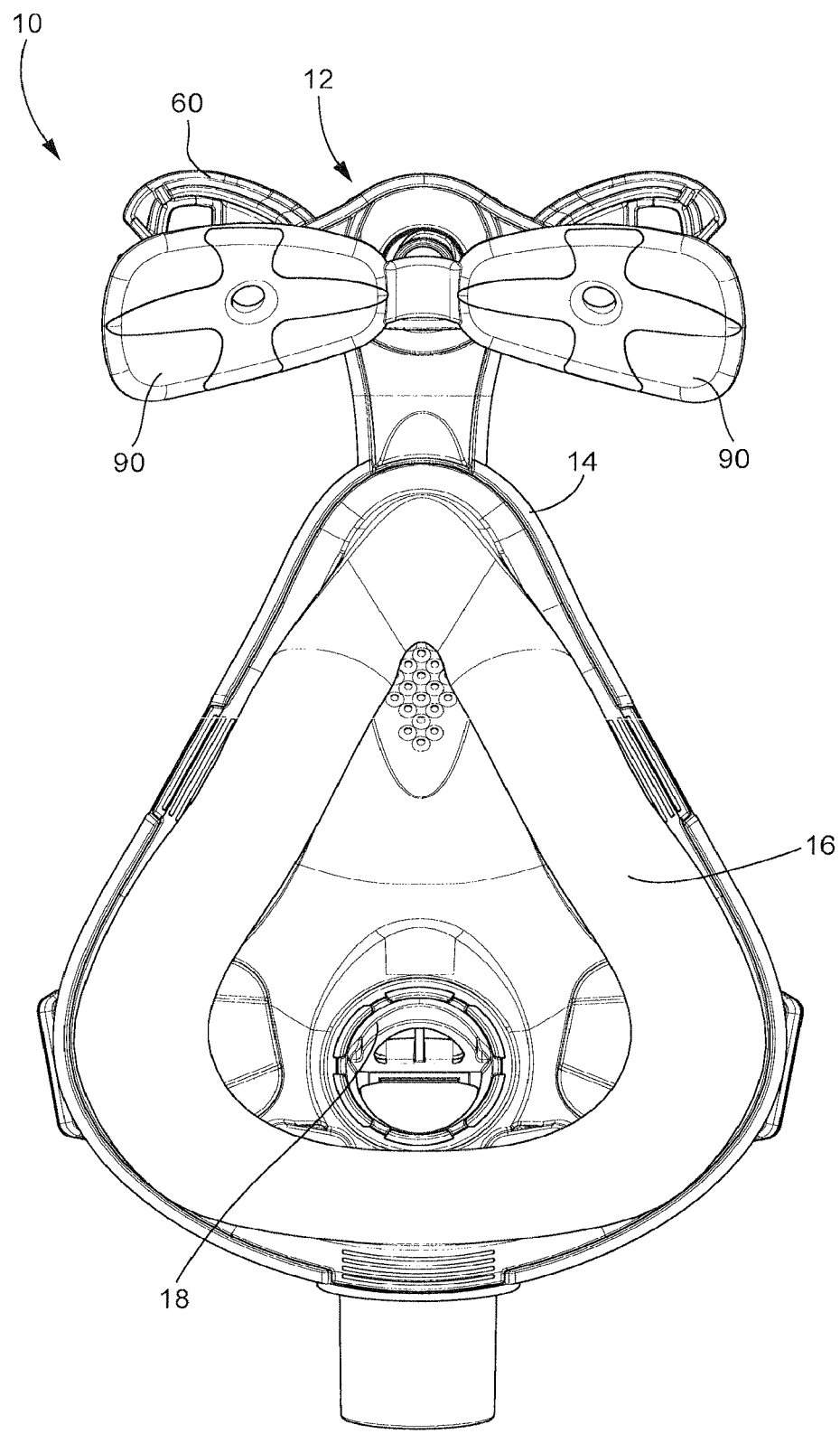

As shown in FIGS. 5-1 to 5-7, the forehead cushion support 60 includes an internally threaded tube 62 joined to forehead cushion support plates 64 that carry forehead cushions 90. As shown in best shown in FIGS. 5-2 and 5-7, the support plates 64 include vertical reinforcing ribs 66 to provide better flexing strength. Also, as best shown in FIG. 5-6, the support plates 64 are angled with respect to the tube 62, e.g., about 15-25°, preferably 21°, from vertical.

The tube 62 includes two splits 68 that divide the tube 62 into two resilient arms 70 which can deflect to allow insertion of the tube 62 into the frame connector 20. In the illustrated embodiment, the splits 68 extend to the cushion support plates 64. However, in an alternative embodiment, the splits 68 may stop at any point along the tube 62 such that they allow sufficient deflection of the tube 62 into the frame connector 20.

The internally threaded tube 62 includes key ways or elongated slots 72 (e.g., three keyways) that receive respective protrusions 22 (e.g., three protrusions) provided on the frame connector 20 (see FIGS. 3-2, 3-3, and 3-5). This arrangement prevents the tube 62, and hence the forehead cushion support 60, from twisting or rotating relative to the frame connector 20. The use of an odd number of key ways 72 also prevents incorrect assembly of the forehead cushion support 60 to the frame connector 20.

As illustrated, a ridge or retention bump 74 is provided at the end of each key way 72. The ridges 74 force the arms 70 to deflect on assembly to the frame connector 20 and prevent inadvertent disassembly of the forehead cushion support 60 from the frame connector 20. In the illustrated embodiment, a lead-in 75 is provided before each ridge 74 (e.g., ridge 74 is spaced inwardly from the end of the tube 62, e.g., by 5 mm) to aid alignment in assembly.

In the illustrated embodiment, the forehead cushion support plates 64 include slots 76 for attaching headgear straps. The headgear straps may include Velcro for length adjustment. A gap 78 is provided in each support plate 64 to allow the headgear strap to be fitted without undoing the Velcro and losing the correct headgear length. This arrangement facilitates assembly and disassembly of the headgear straps from the forehead cushion support plates 64.

In an embodiment, the width of the slots 76 for the headgear straps is preferably 6 mm, and not more than 8 mm. This width constrains the headgear straps to prevent excessive movement of the straps relative to the slots 76.

It is noted that the forehead cushion support plates 64 may include other suitable structures for engaging headgear straps, e.g., clip receiving structures for engaging headgear clips.

The forehead cushion support 60 may be relatively thick and wide in some regions, e.g., wider upper wall 80 as shown in FIG. 5-3, to provide more strength in bending and twisting of the forehead cushion support plates 64.

1.2 Adjustment Knob

As shown in FIGS. 4-1 to 4-7, the adjustment knob 40 includes a threaded shaft 42. In the illustrated embodiment, the threaded shaft 42 and the adjustment knob 40 are integrally formed, e.g., integrally molded, as a one-piece component. However, the adjustment knob 40 and the threaded shaft 42 may be constructed in two parts and permanently or semi-permanently assembled, e.g., by an adhesive. In the illustrated embodiment, the threaded shaft 42 includes a two-start design.

The knob 40 has two half oval finger grips 44 that make the knob 40 easier to operate. The knob 40 also has two external ridges 46 that are diametrically opposed from one another. These ridges 46 may be used as a visual and kinesthetic means of aligning the knob 40 such that the correct forehead support position may be achieved. For example, the ridges 46 may be used to indicate start/finish positions, thereby providing tactile feedback. In the illustrated embodiment, the two-start threads of the threaded shaft 42 align with the two ridges 46 so that when the knob 40 is completely wound, the two ridges 46 extend generally vertically.

In an alternative embodiment, one single ridge may be used to indicate the position of the knob 40. Since the knob 40 may be assembled in two orientations 180 degrees out of phase, i.e., due to two-start threaded shaft 42, the ridge may begin at the top or the bottom.

The adjustment knob 40 clips onto the frame connector 20 with a snap-fit. Specifically, the knob 40 includes a segment 48 that is inserted into the frame connector 20. An annular rim 50 is provided on the segment 48 that can be engaged with retention features 24 provided in the frame connector 20 (see FIGS. 3-1 and 3-3). The segment 48 includes two splits 49 that divide the segment 48 into two resilient arms 52 which can deflect to allow the rim 50, and hence the knob 40, to snap into and out of engagement with the retention features 24. It is noted that the annular rim 50 is thicker as it approaches the splits 49, which allows for an even force to snap the knob 40 on/off regardless of the knob's orientation. Also, the grips 44 and/or ridges 46 facilitate assembly and disassembly of the knob 40 to the frame connector 20.

The threaded shaft 42 is adapted to engage within the internally threaded tube 62 of the forehead cushion support 60 such that the threaded shaft 42 is intermeshed with the internally threaded tube 62. When the knob 40 is rotated, the internally threaded tube 62 extends or retracts from the threaded shaft 42 which causes adjustable movement of the forehead cushions 90.

A resilient prong 54 including a ratchet bump 56 is located within each of the two splits 49 in the adjustment knob 40. When the knob 40 is assembled to the frame connector 20, the ratchet bumps 56 engage a series of ridges 26 around the interior surface of the frame connector 20 (see FIGS. 3-1 and 3-3). The bump/ridge engagement provides tactile feedback in use as described below.

As best shown in FIG. 4-7, the ratchet bump 56 is angled by a with respect to a vertical axis, e.g., 5-6 degrees. The bump 56 is angled so that when the prong 54 and bump 56 thereof is deflected upon assembly to the frame connector 20, an even load will be placed on the face of the bump 56. This allows more even wear on the face of the bump 56.

As best shown in FIGS. 4-3 and 4-4, each prong 54 also has an hourglass or "waisted" shape to help reduce stress on the prong 54 and prevent breakage of the prong 54 from the knob 40. The waist allows a bending force to be more evenly distributed along the length of the prong 54, rather than being concentrated at the proximal end of the prong 54.

In addition, the knob 40 includes a plurality of horns 58, e.g., four horns, around an upper periphery of the segment 48. The four horns 58 facilitate centering of the knob 40 within the frame connector 20. Specifically, the horns 58 rest on an annular surface 28 within the frame connector 20 (see FIGS. 3-1 and 3-3) which acts as a smooth bearing surface.

In an embodiment, the adjustment knob 40 is constructed of a clear microcrystalline polyamide 12, e.g. clear Nylon 12, which is a different material than the other parts of the forehead support, e.g., polycarbonate. This arrangement reduces noise, e.g., squeak, that would occur if two polycarbonate components were used. In addition, clear microcrystalline polyamide 12 has the advantage of being clear.

1.3 Frame Connector

As noted above and best shown in FIGS. 3-1 to 3-6, the frame connector 20 includes retention features 24 for mounting the knob 40, a series of ridges 26 that engage bumps 56 provided on prongs 54 of the knob 40, an annular surface 28 that engages the horns 58 of the knob 40, and three protrusions 22 for guiding the tube 62 of the forehead cushion support 60. An outer housing 21 and an inner housing 23 are also depicted.

In the illustrated embodiment, the ridges 26 include twelve crests and troughs that engage the bumps 56 provided on prongs 54 of the knob 40. As the knob 40 is rotated, the bumps 56 ratchet or click against the ridges 26 to provide indexed incremental adjustment of the forehead support and to provide tactile feedback as to the location of the forehead support. In addition, the bumps 56 help to maintain the position of the forehead support, e.g., prevent self-winding. That is, the bumps 56 will be seated within respective ridges 26 to assist in restraining the forehead support at the desired position. In an embodiment, each click represents 1 mm of travel, with a total of 24 mm of travel available, i.e., two rotations.

As best shown in FIGS. 1-3, 1-4, 1-9, 2-6, and 3-6, the frame connector 20 has a cut-out 30 at its rear which allows the upper portion of the tube 62 to be visible. This arrangement allows markings or position labeling to be added to the tube 62 to indicate the position of the forehead cushion support 60. Position markings are described in greater detail below.

2. Second Illustrated Embodiment of Forehead Support

FIGS. 6-1 to 9-8 illustrate a forehead support 212 and/or associated components, according to another embodiment of the present invention. The forehead support 212 includes a frame connector 220 provided to the mask frame 14 (see FIGS. 6-1 to 6-7), an adjustment knob 240 including a threaded shaft 242 (see FIGS. 7-1 to 7-8), and a forehead cushion support 260 including an internally threaded tube 262 (see FIGS. 8-1 to 8-7). Assembly (see FIGS. 9-1 to 9-8) and operation of the forehead support 212 is substantially similar to the forehead support 12 described above.

2.1 Forehead Cushion Support

Figures 1, 2, 3, 4, 5, 6, 7:
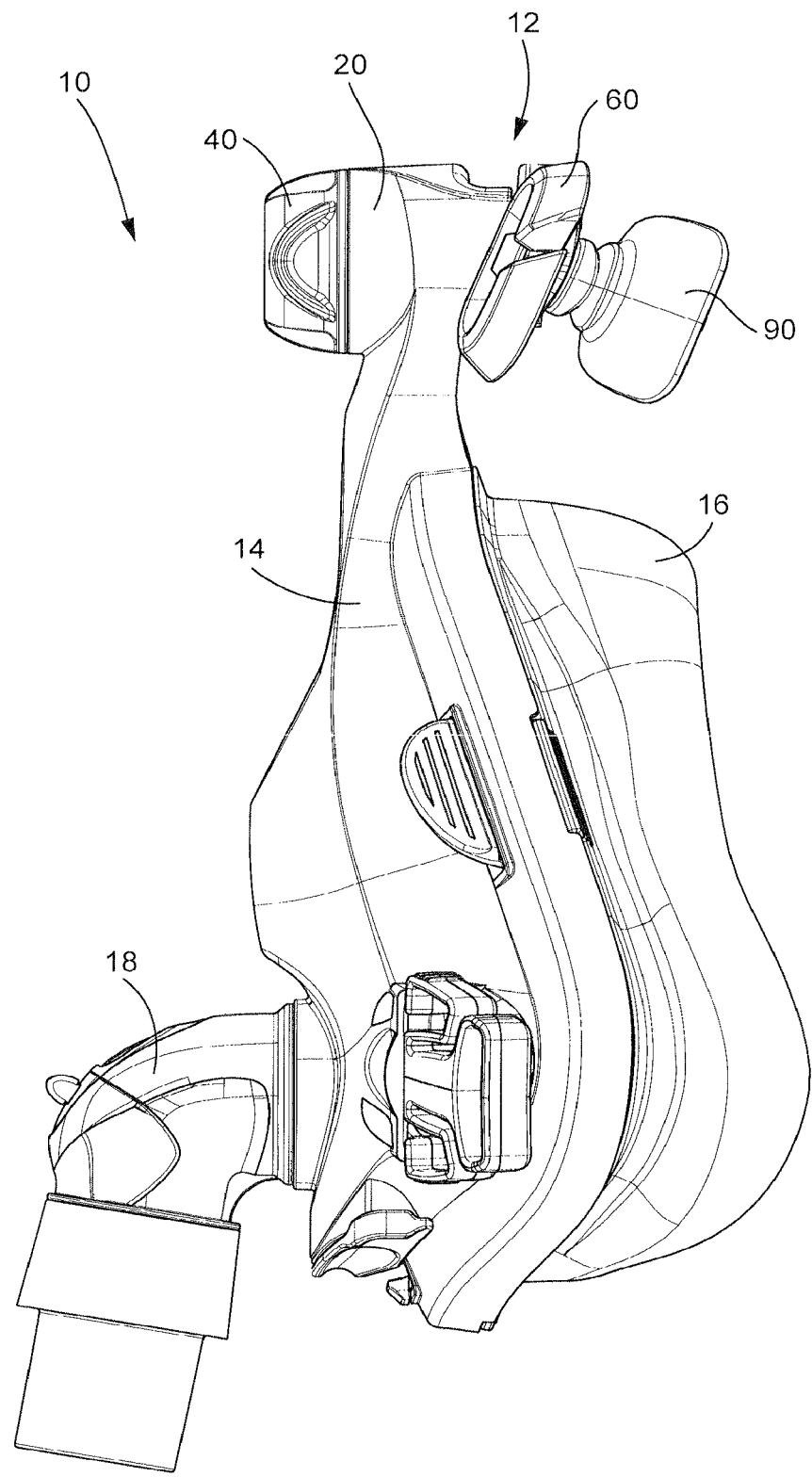
Figures 1, 2, 3, 4, 5, 6, 7, 8:
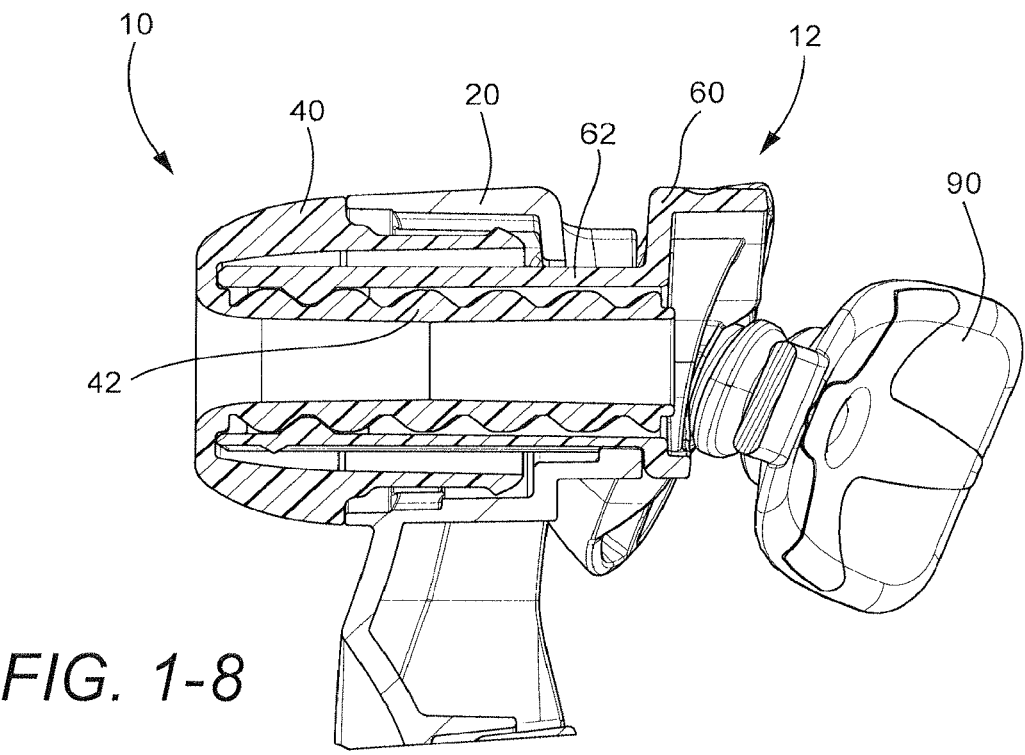

As shown in FIGS. 8-1 to 8-7, the forehead cushion support 260 includes an internally threaded tube 262 (e.g., see threads 263 in FIG. 8-1) joined to forehead cushion support plates 264 that carry forehead cushions. As best shown in FIGS. 8-2 and 8-4, the support plates 264 include horizontal reinforcing ribs 266 to provide better flexing strength. Also, as best shown in FIG. 8-5, the support plates 264 are angled with respect to the tube 262, e.g., about 15-25°, or preferably 21°, from vertical.

The tube 262 includes two splits 268 that divide the tube 262 into two resilient arms 270 which can deflect to allow insertion of the tube 262 into the frame connector 220. In the illustrated embodiment, the splits 268 extend to the cushion support plates 264.

The internally threaded tube 262 includes key ways or elongated slots 272 (e.g., three keyways) that receive respective protrusions 222 (e.g., three protrusions) provided on the frame connector 220 (see FIGS. 6-2 to 6-7). Three hole 265 are provided in the support plates 264 at the end of the key ways 272. The three holes 265 allow the three protrusions 222 on the frame connector 220 to protrude through the support plates 264 when the forehead cushion support 260 is retracted (e.g., see FIGS. 9-2, 9-3, and 9-5). This arrangement provides a longer, more stable attachment.

As illustrated, a ridge or retention bump 274 is provided at the end of each key way 272. The ridges 274 force the arms 270 to deflect on assembly to the frame connector 220 and prevent inadvertent disassembly of the forehead cushion support 260 from the frame connector 220. In the illustrated embodiment, the ridges 74 are provided at the end of the tube 262, i.e., no lead-in as in the forehead cushion support 60.

In the illustrated embodiment, the forehead cushion support plates 264 include slots 276 for attaching headgear straps. The headgear straps may include Velcro for length adjustment. A gap 278 is provided in each support plate 264 to allow the headgear strap to be fitted without undoing the Velcro and losing the correct headgear length. This arrangement facilitates assembly and disassembly of the headgear straps from the forehead cushion support plates 264.

In the illustrated embodiment, the width of the slots 276 is wider than those of the forehead cushion support 60. However, other suitable widths are possible. Also, the forehead cushion support 260 may be thinner in some regions when compared to the forehead cushion support 60, e.g., upper wall 280 of forehead cushion support 260 is thinner than that of the forehead cushion support 60 (see FIG. 8-6).

2.2 Adjustment Knob

Referring to FIGS. 7-1 to 7-8, the adjustment knob 240 is substantially similar to the adjustment knob 40 described above. In contrast, each prong 254 does not have an hourglass or "waisted" shape such as that of the prong 54 (see FIGS. 7-5 and 7-6).

As noted above, the ratchet bump 256 of each prong 254 is angled at a with respect to a vertical axis, e.g., 5-6 degrees. This arrangement is more clearly shown in FIG. 7-4.

2.3 Frame Connector

As shown in FIGS. 6-1 to 6-7, similar to the frame connector 20 described above, the frame connector 220 includes retention features 224 for mounting the knob 240, a series of ridges 226 that engage bumps 256 provided on prongs 254 of the knob 240, an annular surface 228 that engages the horns 258 of the knob 240, and three protrusions 222 for guiding the tube 262 of the forehead cushion support 260.

As illustrated, the three protrusions 222 protrude from the frame connector 220, which provides a stable connection with the forehead cushion support 260. This arrangement is in contrast to that of the frame connector 20 in which the protrusions were provided at an interior portion of the frame connector 20.

3. Position Markings on Forehead Support

In an embodiment, position markings may be provided on the tube of the forehead cushion support, the frame connector, and/or the adjustment knob to indicate the forehead support's position.

3.1 Position Markings on Tube

An indicator, e.g., artwork or graphics, may be added to the tube to indicate the 24 positions of the adjustment knob (e.g., each click of knob represents 1 mm of travel, with a total of 24 mm of travel available, so 24 clicks or positions). The artwork may be achieved by pad-printing (after molding). Other options for providing artwork on the tube include etching, laser-etching, and in-mould decoration (where the artwork is pre-printed on polycarbonate, die-cut, and put into the mold prior to molding).

Figures 1, 2, 3, 4, 5, 6, 7, 8, 9:
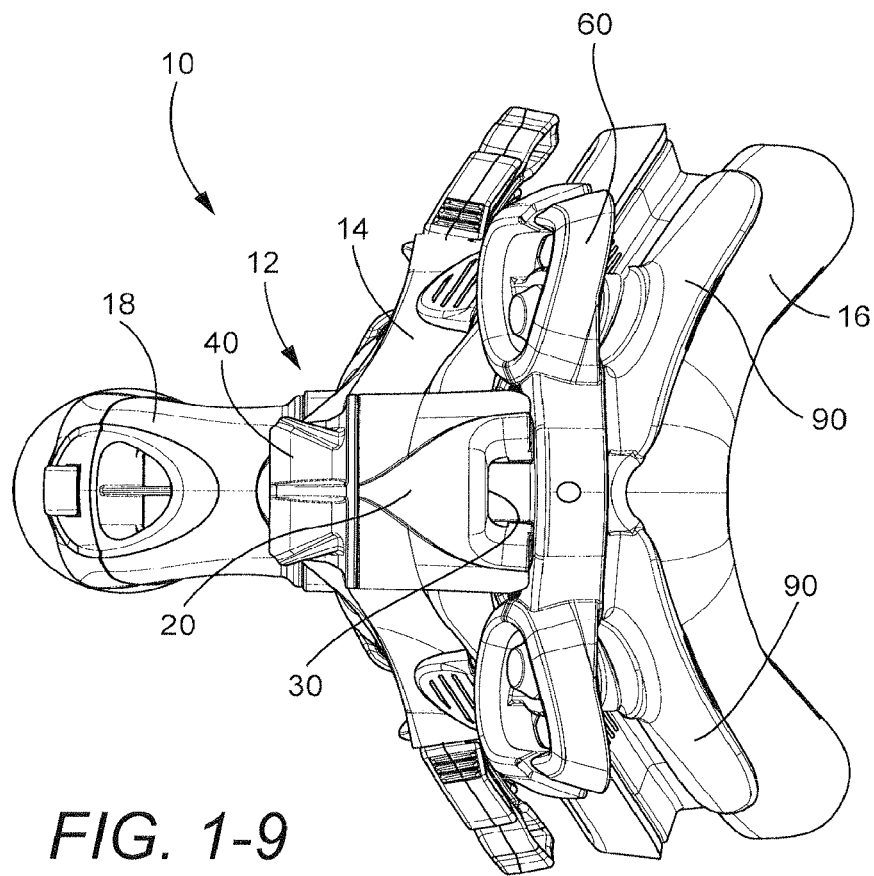
Figures 1, 2, 3, 4, 5, 6, 7, 8, 9, 10:
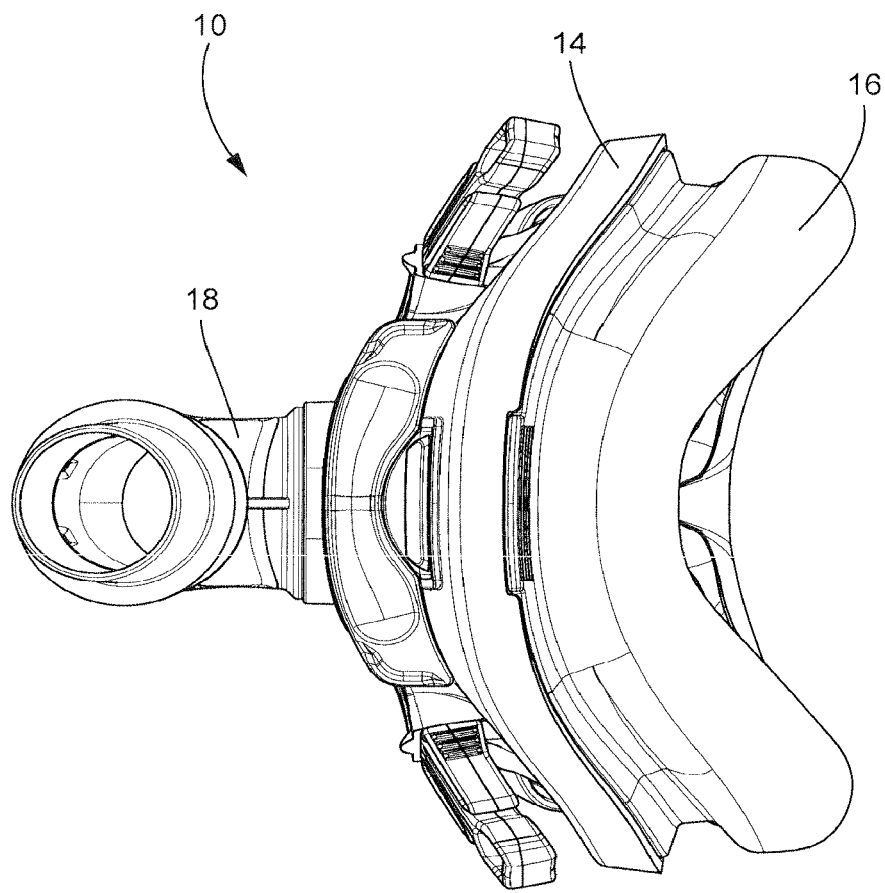
Figure 2:
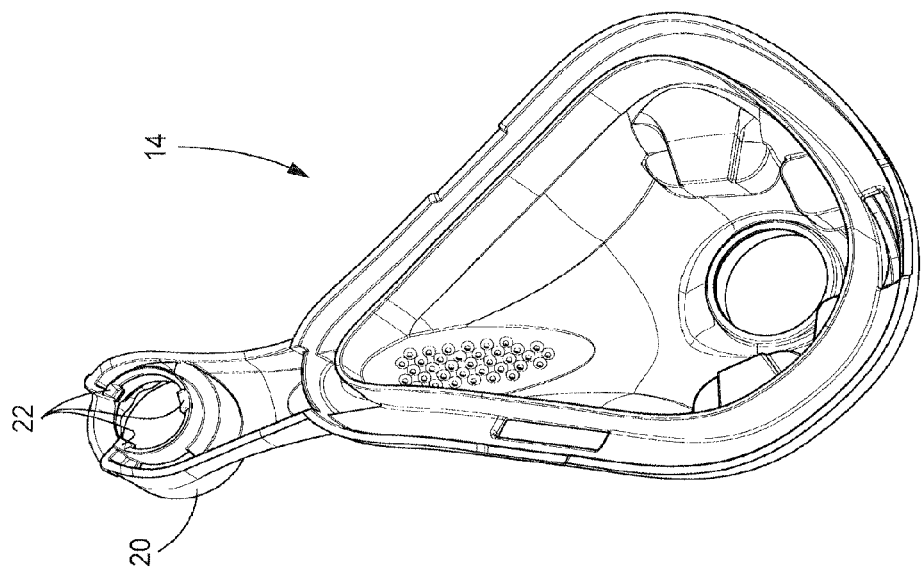
Figures 1, 2:
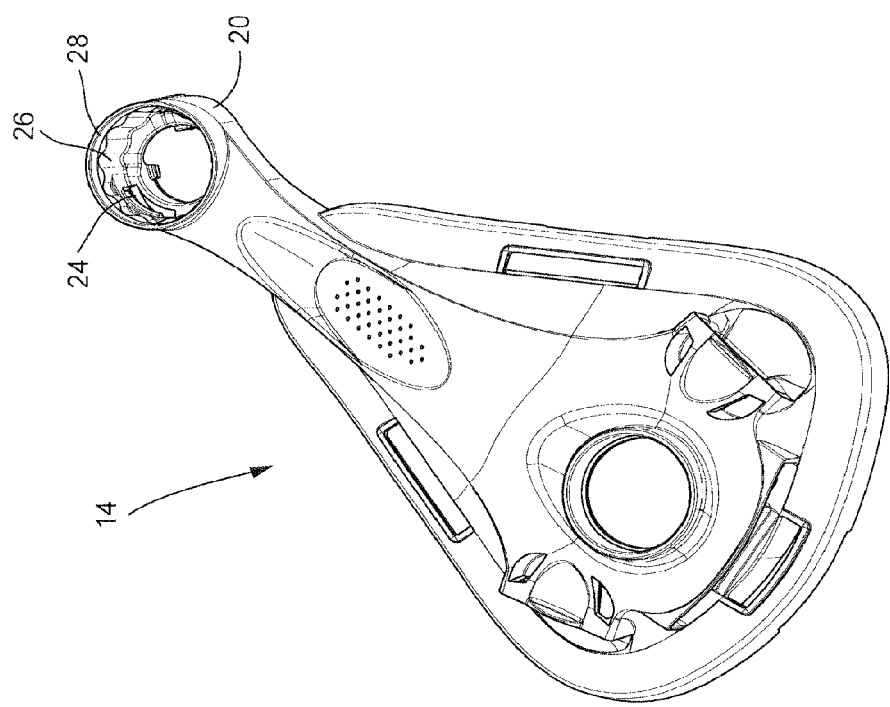
Figures 2, 3, 4:
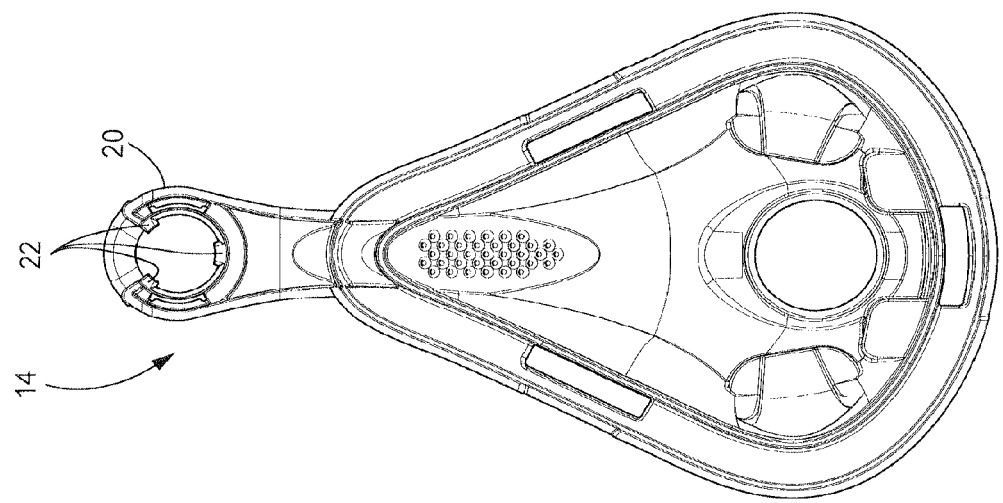
Figures 2, 3:
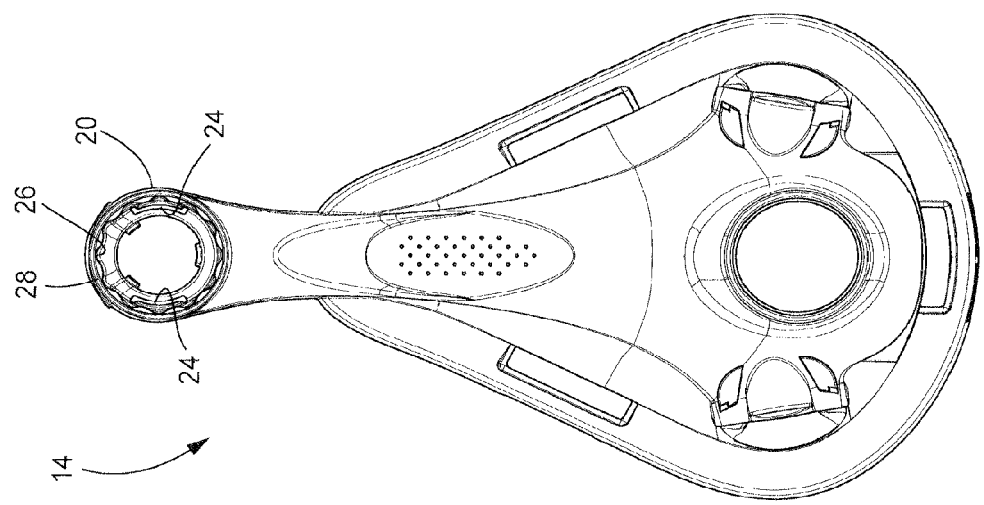
Figures 2, 3:
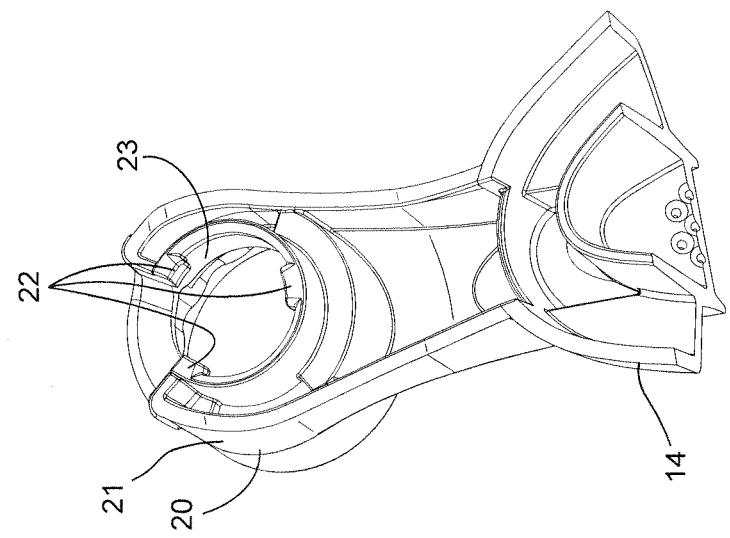
Figures 1, 3:
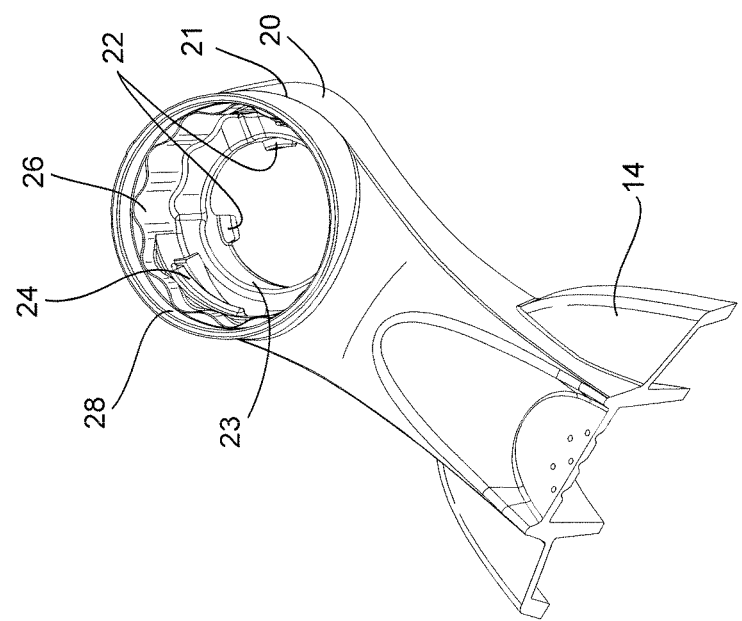
Figures 3, 4, 5:
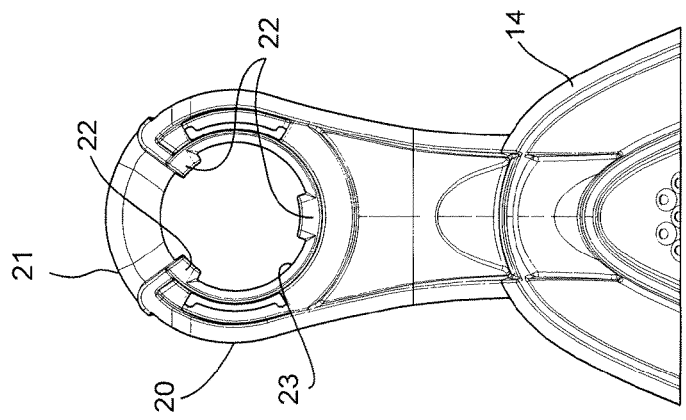
Figures 3, 4:
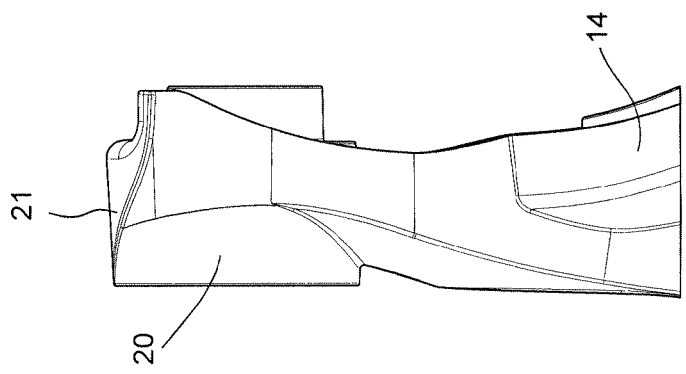
Figures 3, 4, 5, 6:
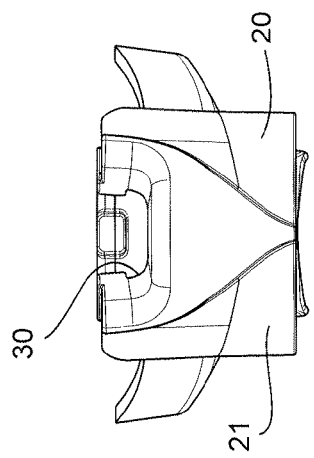
Figure 3:
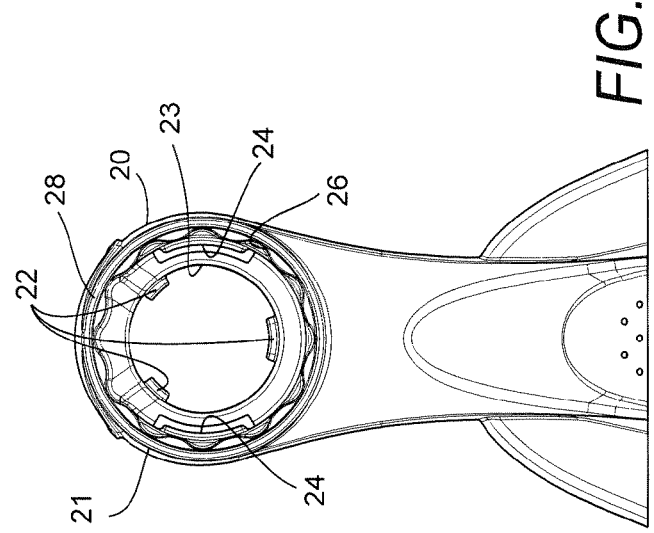
Figures 2, 4:
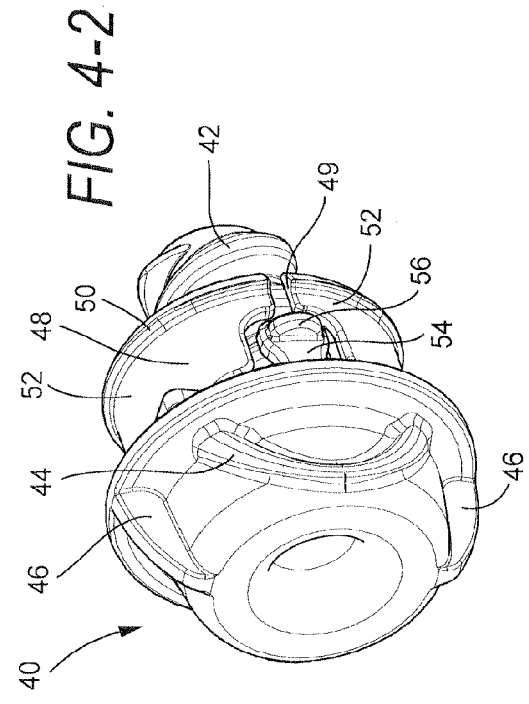
Figure 4:
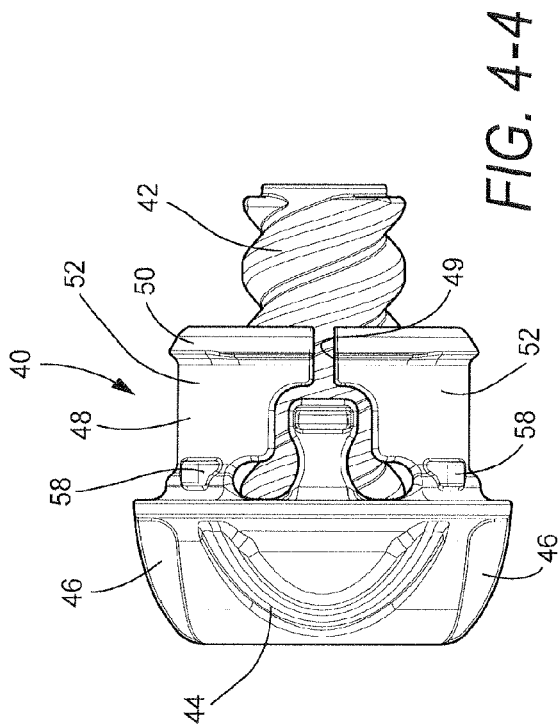
Figures 1, 4:
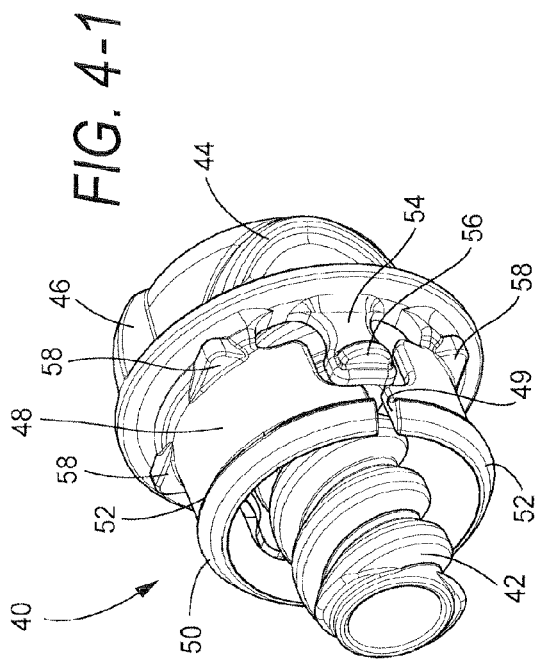
Figures 3, 4:
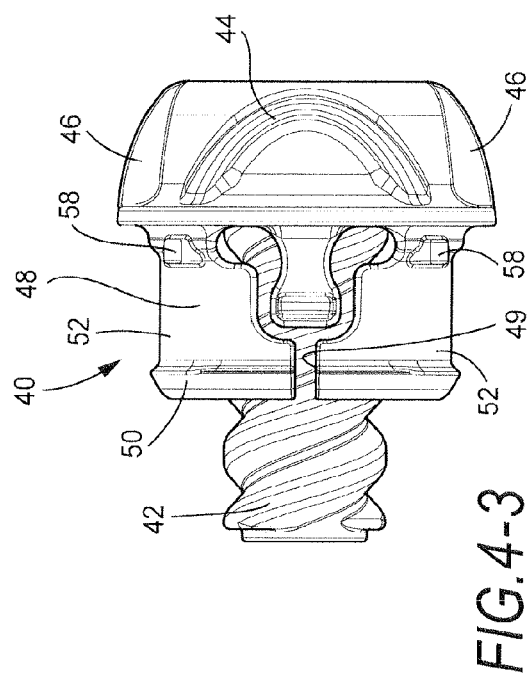
Figures 3, 6:
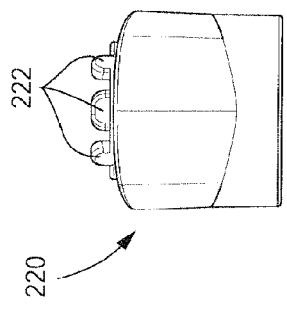
Figures 4, 6:
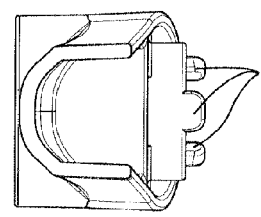
Figures 6, 7:
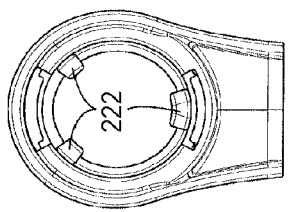
Figures 2, 6:
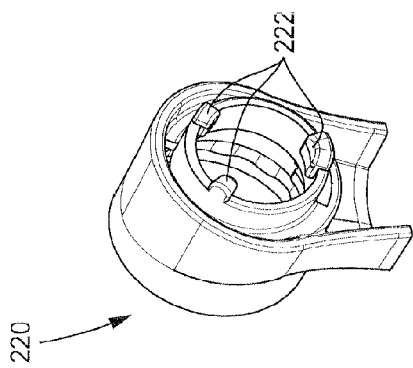
Figure 6:
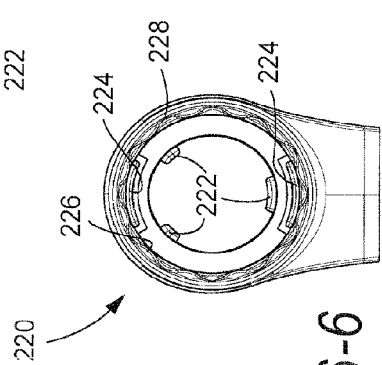
Figures 1, 6:
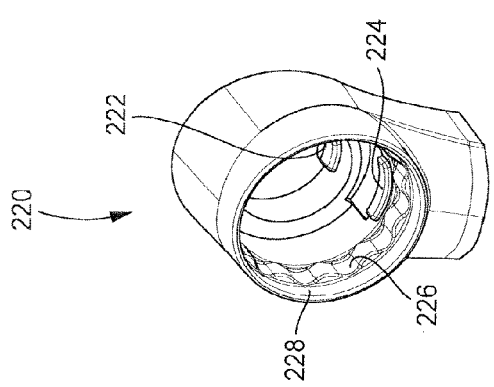
Figures 5, 6:
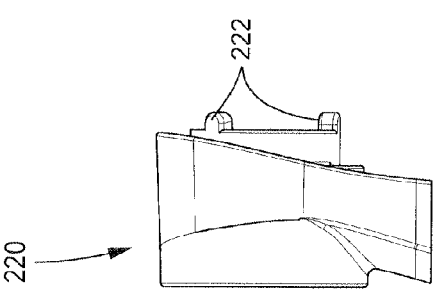
Figures 2, 7:
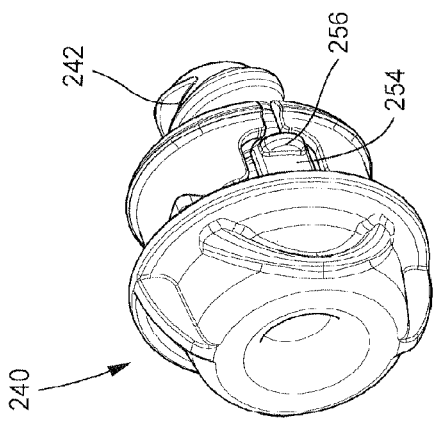
Figures 3, 7:
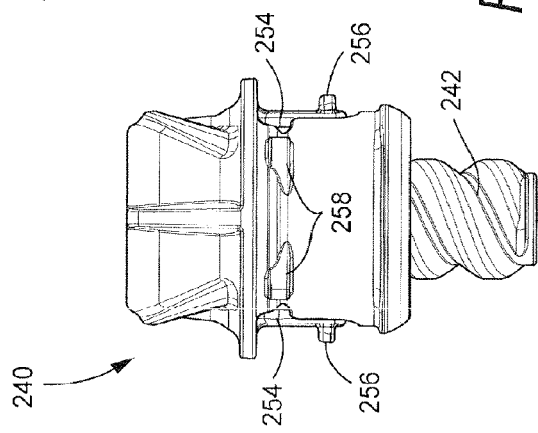
Figures 1, 7:
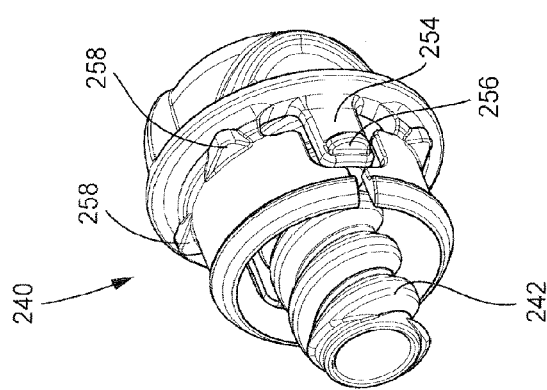
Figures 4, 7:
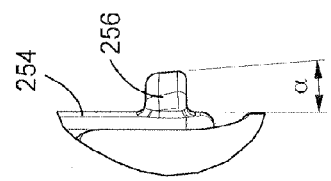
Figure 7:
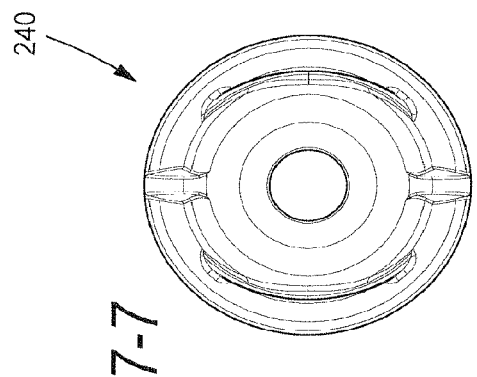
Figures 7, 8:
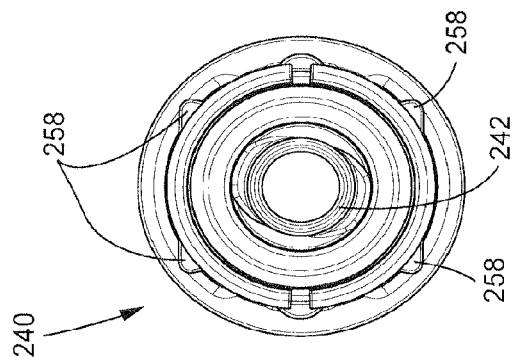
Figures 6, 7:
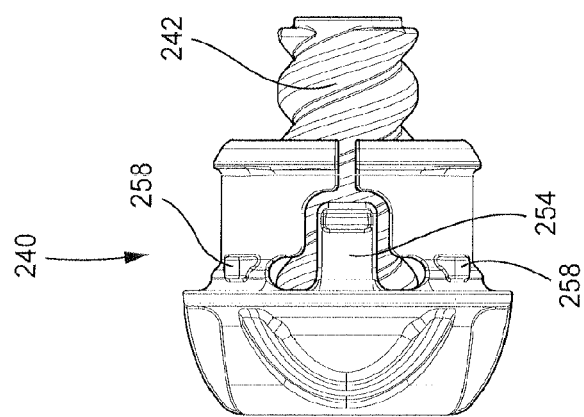
Figures 5, 7:
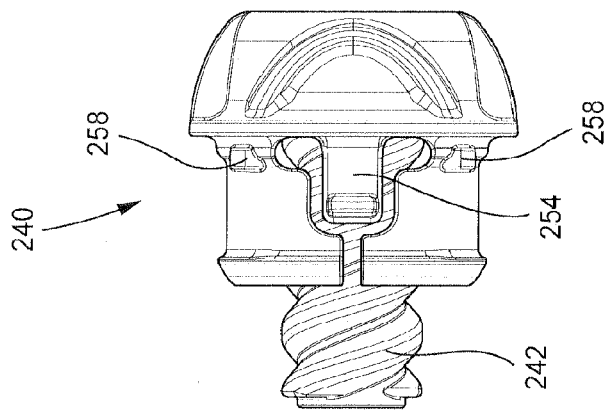
Figures 2, 8:
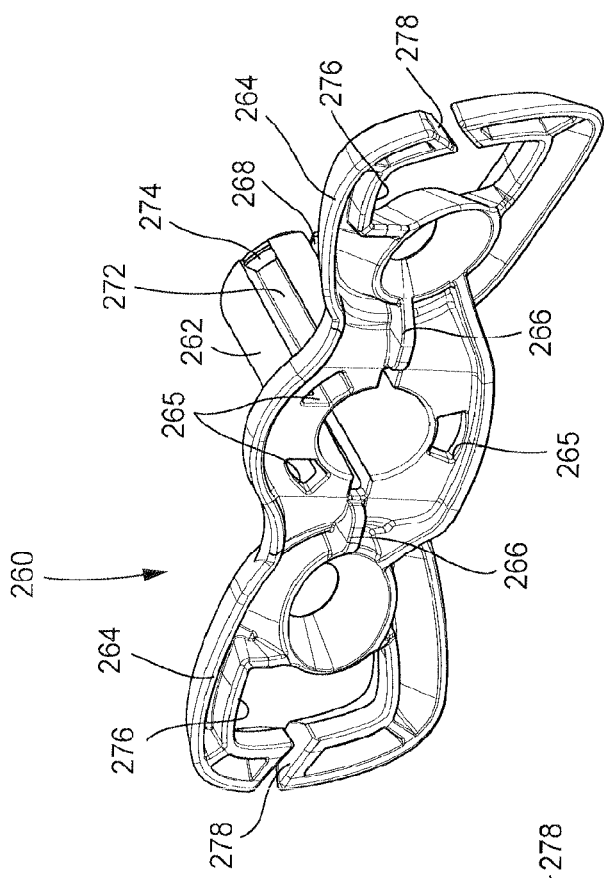
Figures 1, 8:
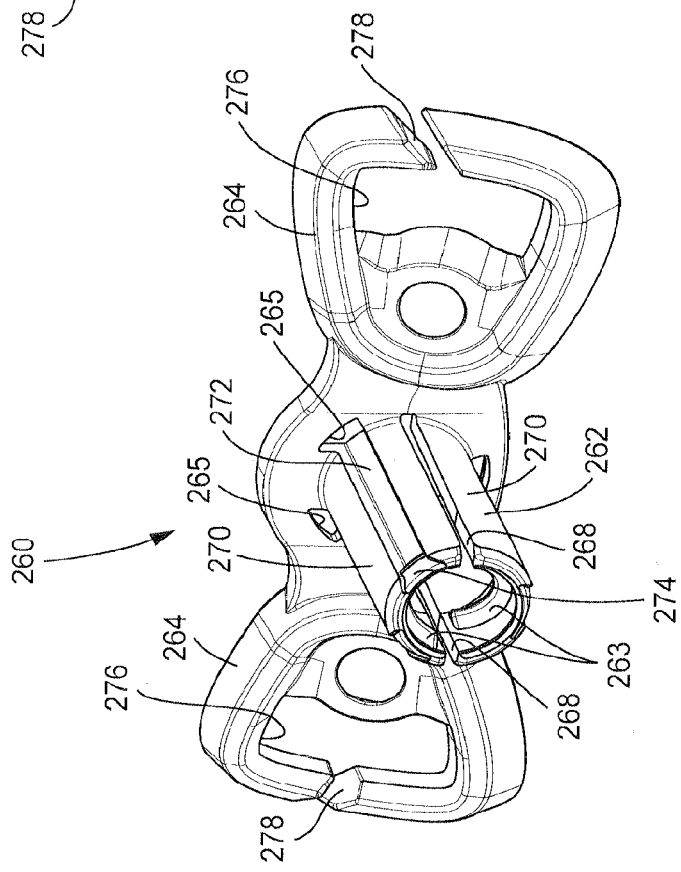
Figures 5, 8:
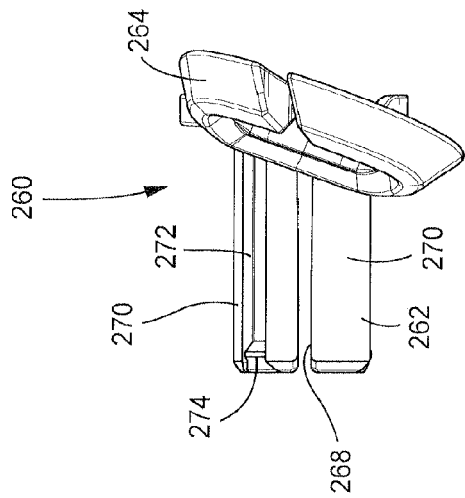
Figures 3, 8:
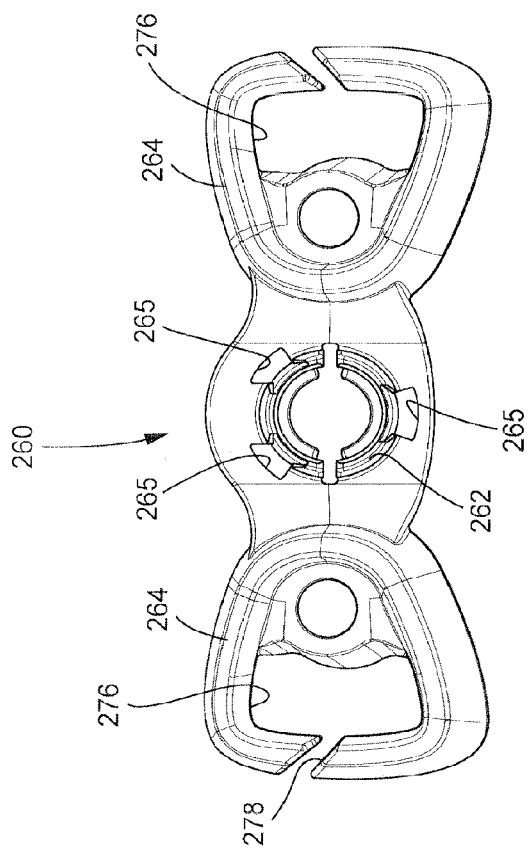
Figures 4, 8:
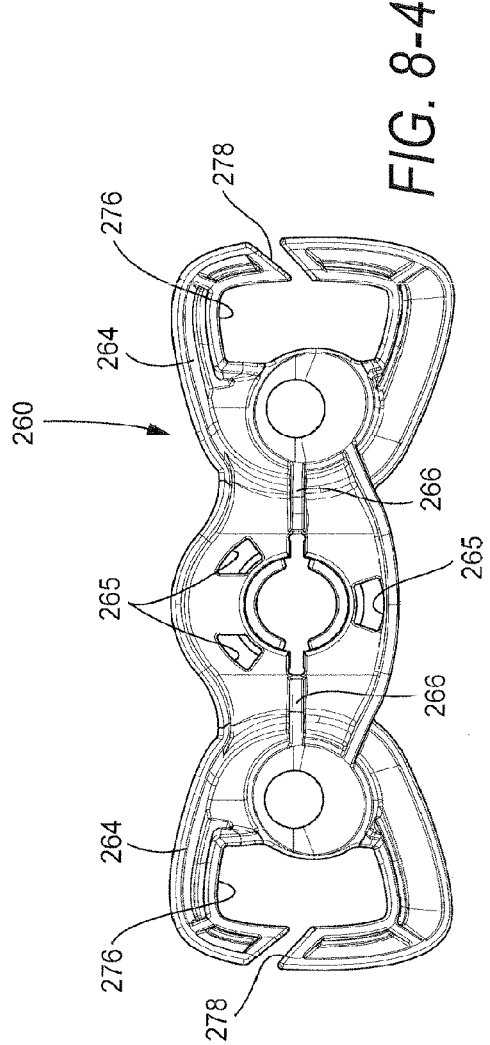
Figures 2, 9:
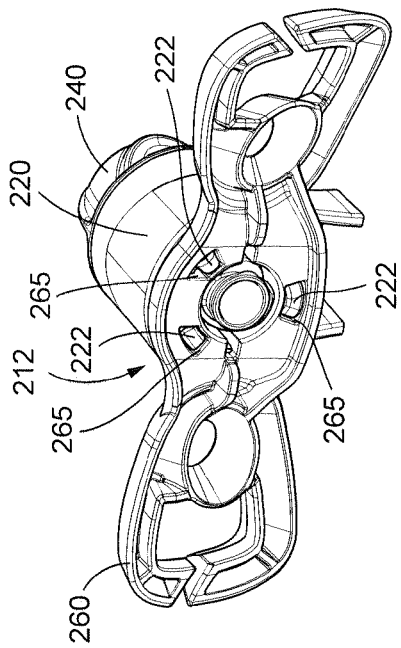
Figures 3, 9:
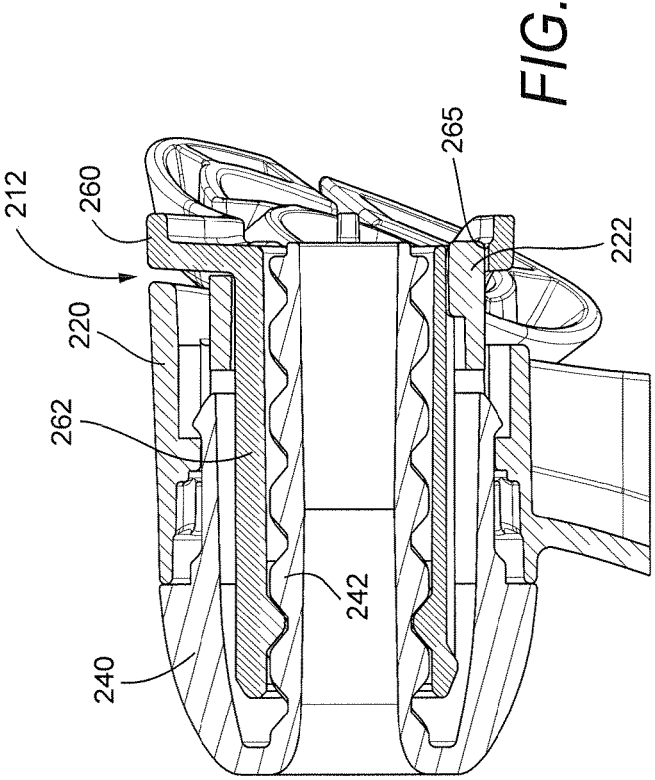
Figures 1, 9:
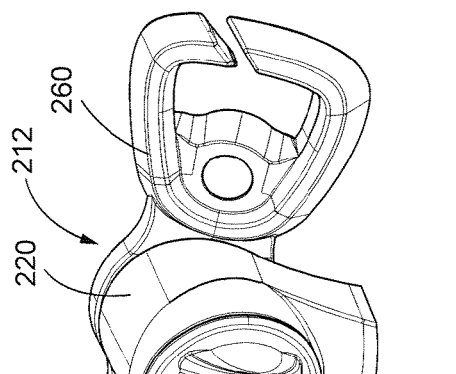
Figures 1, 10:
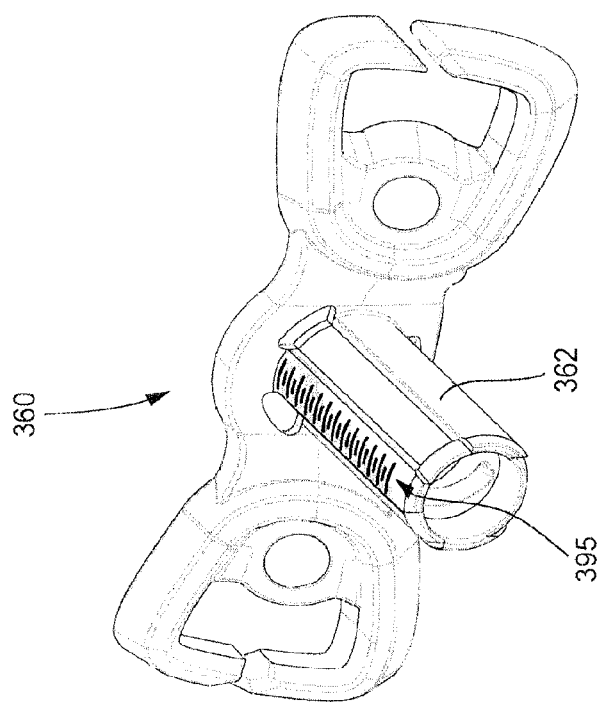
Figures 5, 10:
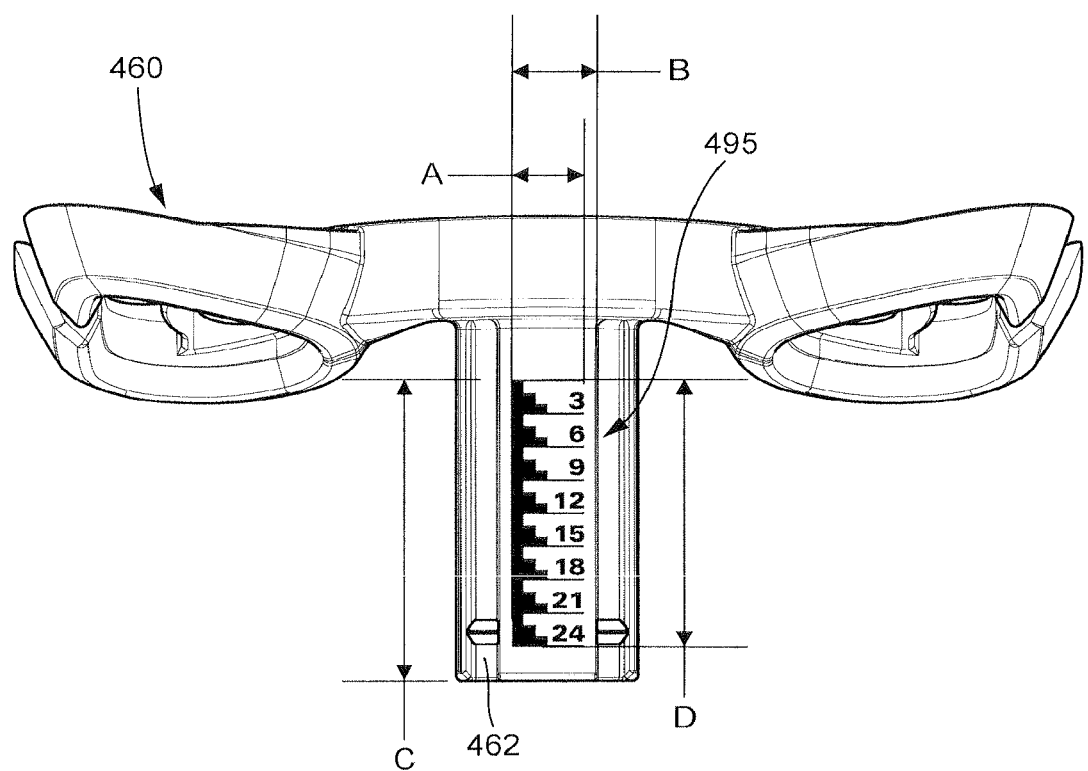

FIG. 10-1 illustrates a forehead cushion support 360 having a tube 362 with localized in-mold decoration 395. As illustrated, the in-mold decoration 395 includes spaced markings to indicate the forehead support's position as the tube 362 is extended and retracted during use. The markings may extend along full length of the tube 362 and provide a high resolution.

FIGS. 10-2 to 10-4 illustrate forehead cushion supports 460, 560, 660 including tubes 462, 562, 662 with different embodiments of pad printed artwork 495, 595, 695. As illustrated, the artwork 495, 595, 695 includes spaced markings, which are numbered, to indicate the forehead support's position as the tube is extended and retracted during use. In the illustrated embodiment, 24 markings or steps are provided, which are numbered every three positions. This artwork provides a series of steps which is easily understood by the user. The forehead cushion supports 460, 560, 660 are all shown in the "24" or fully extended position. The current position aligns with the bottom of the respective cut-out 430, 530, 630 in the frame connector.

However, other suitable markings may be provided on the tube, e.g., simple lines or alphabetical labeling.

FIG. 10-5 illustrates exemplary dimensions for the forehead cushion support 460 with artwork 495. In an embodiment A may be 5.75-6.25 mm, e.g., 6.0 mm, B may be 6.6-7.6 mm, e.g., 7.1 mm, C may be 26.2-28.2 mm, e.g., 27.2 mm, and D may be 23.95-23.45 mm, e.g., 24.2 mm. Although specific dimensions and ranges are provided, it is to be understood that these dimensions and ranges are merely exemplary and other dimensions and ranges are possible depending on application. For example, ranges that vary from those provided +/−10% may be suitable for particular applications.

3.2 Position Markings on Frame Connector and/or Adjustment Knob

Position markings may be provided to the frame connector and/or the adjustment knob to indicate the forehead support's position.

3.2.1 First Illustrated Embodiment

Figures 3, 11:
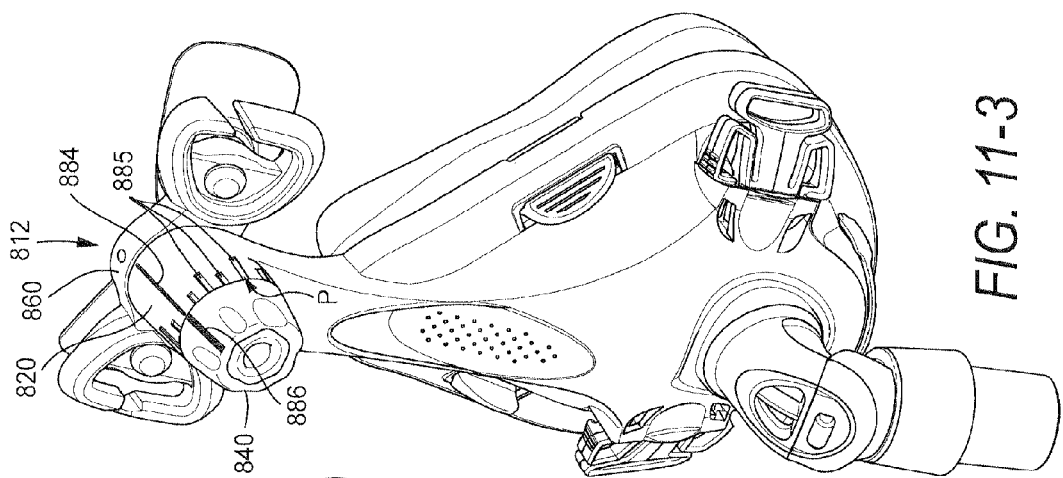
Figures 2, 11:
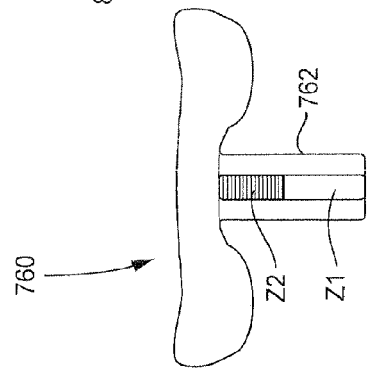
Figures 1, 11:
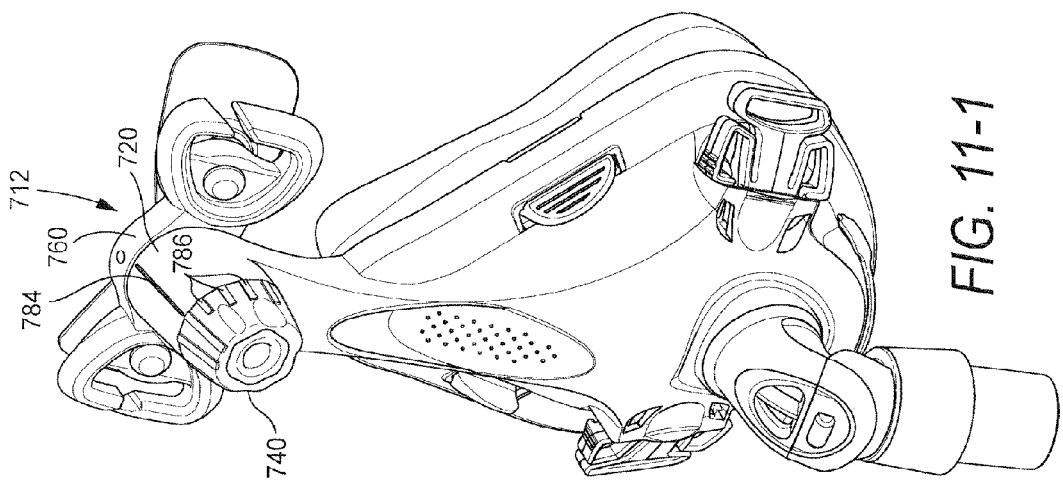
Figures 7, 11:
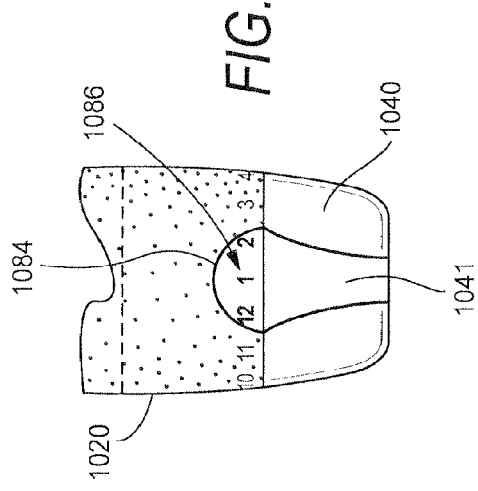
Figures 9, 11:
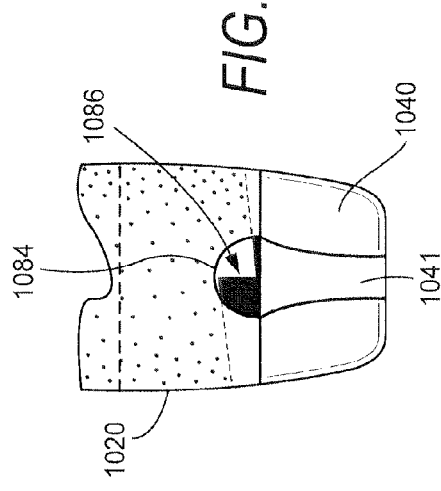
Figures 8, 11:
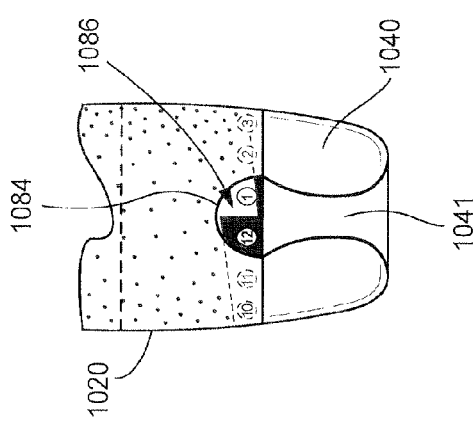
Figures 10, 11:
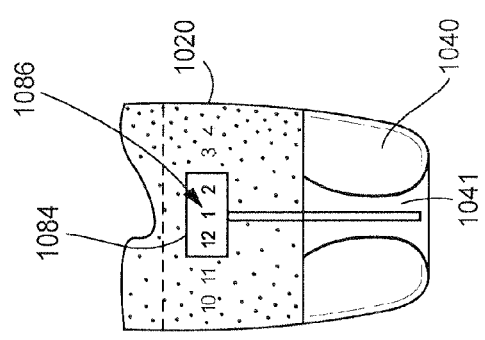

FIG. 11-1 illustrates an embodiment of a forehead support 712 wherein the frame connector 720 includes a single line 784 on the top thereof and the adjustment knob 740 includes ascending bumps 786 around its perimeter. During use, a selected one of the ascending bumps 786 on the knob 740 can be aligned with the line 784 on the frame connector 720 to indicate the forehead support's position.

In an embodiment, the bumps 786 on the knob 740 may be formed during molding of the knob 740 in the molding tool and the single line 784 may be printed on the frame connector 720, e.g., by pad printing, in any suitable color, e.g., blue. This arrangement provides position markings that are relatively simple to implement.

The ascending or varying height bumps 786 on the knob 740 provide grip for turning as well as tactile feedback of the knob's position. In addition, alignment of the large bump on the knob 740 with the pad printed line 784 on the top of the frame connector 720 (as shown in FIG. 11-1) allows the knob 740 to be assembled and calibrated correctly.

In an embodiment, the forehead cushion support 760 may include a two-zone marking that indicates whether one is on the first rotation or the second rotation of the knob 740. For example, as shown in FIG. 11-2, the tube 762 of the forehead cushion support 760 may include a label on the top edge thereof that defines a first zone Z1 having a first color, e.g., white, and a second zone Z2 having a second color different than the first color, e.g., blue. Each color represents a full rotation of the knob 740 in use, e.g., 360°. That is, the tube color indicates whether the knob is within its first rotation or its second rotation.

3.2.2 Second Illustrated Embodiment

FIG. 11-3 illustrates an embodiment of a forehead support 812 wherein the frame connector 820 includes a printed line 884 along with textured increment markings 885 around its perimeter. The adjustment knob 840 includes single printed line 886. During use, the line 886 on the knob 840 can be aligned with a selected one of the line 884 or markings 885 on the frame connector 820 to indicate the forehead support's position.

In an embodiment, the lines 884, 886 on the frame connector 820 and knob 840 may be printed thereon, e.g., by pad printing, in any suitable color, e.g., blue. The textured increment markings 885 may be formed during molding of the frame connector 820 for example. This arrangement provides position markings that are relatively simple to implement.

Alignment of the relatively long pad printed line 886 on the knob 840 with the relatively long pad printed line 884 on the top of the frame connector 820 (as shown in FIG. 11-3) allows the knob 840 to be assembled and calibrated correctly. In addition, it is intuitive that the two pad printed lines 884, 886, e.g., blue lines, align for correct assembly and calibration.

In an embodiment, the forehead cushion support 860 may include a two-zone marking (such as that shown in FIG. 11-2) that indicates whether the knob 840 is on the first rotation or the second rotation.

The forehead support 812 provides an arrangement that is relatively easy to prescribe a setting. For example, the patient may be prescribed with a "white-2" which would correspond to the position P as the patient turns the knob 840 from the fully open position.

3.2.3 Third Illustrated Embodiment

FIGS. 11-4 and 11-5 illustrate an embodiment of a forehead support 912 wherein the frame connector 920 and the adjustment knob 940 include an asymmetrical shape. As illustrated, the frame connector 920 and knob 940 have an elongated top portion. This arrangement is relatively simple to align, assemble and calibrate the adjustment starting point, e.g., by adjusting the knob 940 until its exterior surfaces are flush with the exterior surfaces of the frame connector 920. In addition, the asymmetrical shape provides good tactile feedback of the knob's position.

3.2.4 Fourth Illustrated Embodiment

FIGS. 11-6 to 11-10 illustrate an embodiment of a forehead support 1012 wherein the frame connector 1020 includes a transparent window 1084 on the top thereof (e.g., fish eye window or gloss window) and the adjustment knob 1040 includes a numeric and/or graphic scale 1086 (see FIGS. 11-7 to 11-10) around its perimeter that is viewable through the window 1084. During use, a selected number and/or graphical position on the scale 1086 of the knob 1040 can be aligned with the window 1084 on the frame connector 1020 to indicate the forehead support's position.

In an embodiment, the exterior surface of the frame connector 1020 surrounding the window 1084 may be textured. Also, the knob 1040 may include a raised portion or rib 1041 to provide grip for turning as well as tactile feedback of the knob's position.

In an embodiment, the numeric and/or graphic scale 1086 on the knob 1040 may be printed thereon, e.g., by pad printing, in any suitable color.

Also, the forehead cushion support 1060 may include a two-zone marking (such as that shown in FIG. 11-2) that indicates whether the knob 1040 is on the first rotation or the second rotation. This arrangement is very prescriptive and allows fine adjustment as there would be a zone indicated by the forehead cushion support 1060 and a number/graphical position in the window 1084.

FIGS. 11-7 to 11-10 illustrate alternative embodiments of the window 1084 on the frame connector 1020 and/or the scale 1086 on the knob 1040. In each embodiment, the scale 1086 is provided on a portion of the knob 1040 that is enclosed by the frame connector 1020 to allow the patient to read the scale 1086 through the window 1084.

In FIG. 11-7, the scale 1086 includes numbers and an ascending height band to indicate the forehead support's position. In FIG. 11-8, the window 1084 is positioned more inwardly on the frame connector 1020 (with respect to FIG. 11-7), e.g., near the retaining rim of the knob, and the scale 1086 includes only numbers. In FIG. 11-9, the scale 1086 includes only numbers to indicate the forehead support's position. In FIG. 11-10, the scale 1086 includes only an ascending height band to indicate the forehead support's position. However, other suitable scales and window configurations are possible.

3.2.5 Fifth Illustrated Embodiment

FIG. 11-11 illustrates an embodiment of a forehead support 1112 wherein the frame connector 1120 includes increment recesses 1184 around its perimeter and the adjustment knob 1140 includes a clicker 1186 that is adapted to selectively engage with the recesses provided on the frame connector 1120. During use, the clicker 1186 on the knob 1140 can be selectively engaged within one of the recesses 1184 on the frame connector 1120 to indicate the forehead support's position.

As illustrated, the knob 1140 includes a raised portion or rib 1141 to provide grip for turning as well as tactile feedback of the knob's position.

The clicker 1186 and raised portion 1141 provide good positional information that is both visual and tactile. In addition, the clicker 1186 and raised portion 1141 provide an arrangement that is relatively simple to align, assemble, and calibrate the adjustment starting point.

Also, the forehead cushion support 1160 may include a two-zone marking (such as that shown in FIG. 11-2) that indicates whether the knob 1140 is on the first rotation or the second rotation. This allows a setting to be prescribed relatively easily, e.g., clicker setting along with zone on forehead cushion support.

3.2.6 Sixth Illustrated Embodiment

Figures 11, 12:
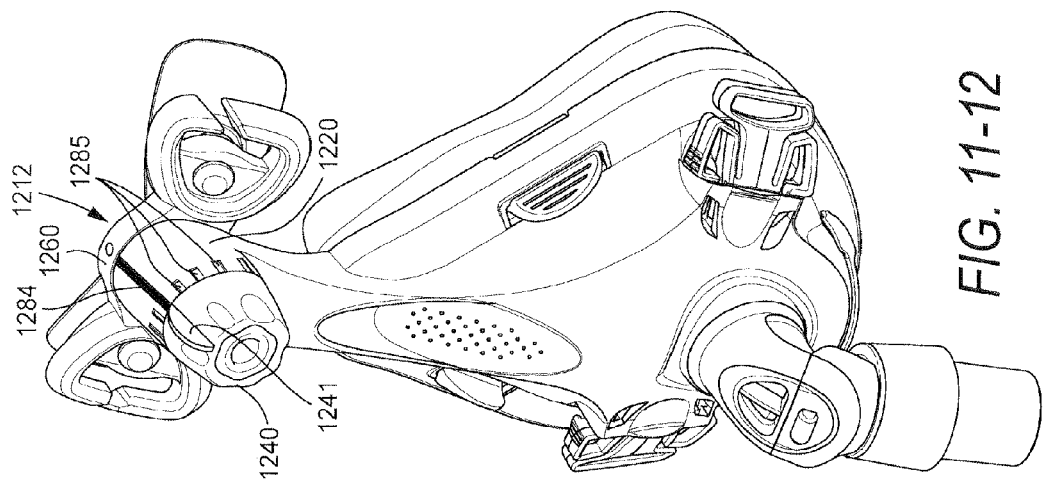
Figures 11, 12, 13:
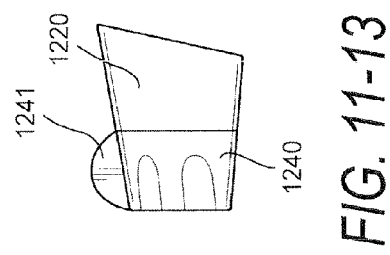
Figure 11:
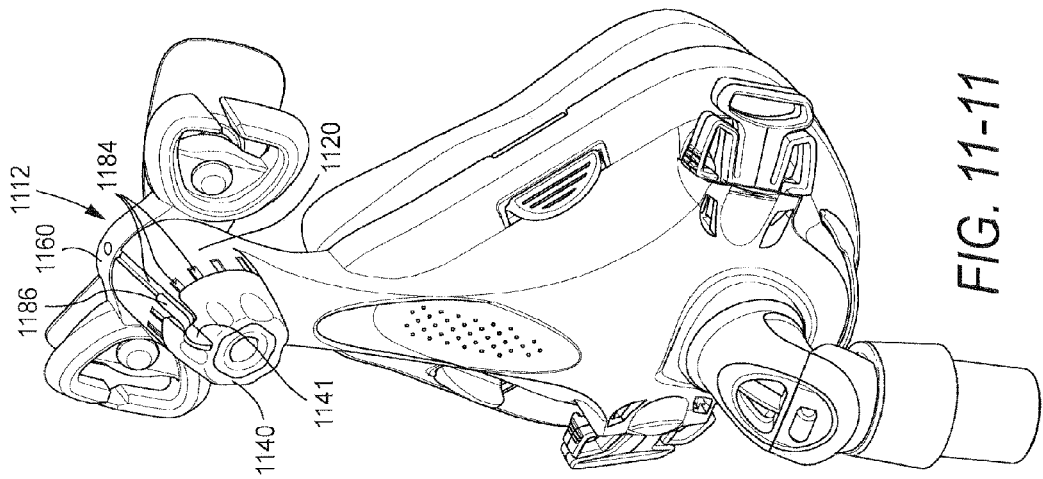

FIGS. 11-12 to 11-13 illustrate an embodiment of a forehead support 1212 wherein the frame connector 1220 includes a printed line 1284 along with etched texture markings 1285 around its perimeter. The adjustment knob 1240 includes a raised portion or rib 1241. During use, the raised portion 1241 on the knob 1240 can be aligned with a selected one of the line 1284 or markings 1285 on the frame connector 1220 to indicate the forehead support's position.

In an embodiment, the line 1284 on the frame connector 1220 may be printed thereon, e.g., by pad printing, in any suitable color, e.g., blue.

The raised portion 1241 on the knob 1240 provides grip for turning as well as tactile feedback of the knob's position. In addition, the raised portion 1241 and relatively long pad printed line 1284 on the top of the frame connector 1220 provide an arrangement that is relatively simple to align, assemble, and calibrate the adjustment starting point.

In an embodiment, the forehead cushion support 1260 may include a two-zone marking (such as that shown in FIG. 11-2) that indicates whether the knob 1240 is on the first rotation or the second rotation.

The forehead support 1212 provides an arrangement that is relatively easy to prescribe a setting, e.g., knob setting along with zone on forehead cushion support.

3.2.7 Seventh Illustrated Embodiment

FIG. 11-14 illustrates an embodiment of a forehead support 1312 wherein the frame connector 1320 includes markings 1384 on the top thereof and the forehead cushion support 1360 includes a depth gauge or position indicator 1386 on the top thereof with a single marking 1387 that is movable relative to the markings 1384 on the frame connector 1320. As illustrated, the position indicator 1386 extends over a top portion of the frame connector 1320 and the marking 1387 is provided on a free end of the position indicator 1386. As the knob 1340 is rotated in use, the position indicator 1386 moves relative to the frame connector 1320 and the marking 1387 on the position indicator 1386 can be aligned with a selected one of the markings 1384 on the frame connector 1320 to indicate the forehead support's position.

In addition, the knob 1340 includes a raised portion or rib 1341 that can be aligned with a selected one of the markings 1385 provided around the perimeter of the frame connector 1320 to indicate the forehead support's position. The raised portion 1341 provides grip for turning as well as tactile feedback of the knob's position. Further, the markings 1385 help ensure that the knob 1340 is in a correct ratchet position and not halfway between.

The raised portion 1341 and position indicator 1386 provide an arrangement that is relatively simple to align, assemble, and calibrate the adjustment starting point. Also, due to the position indicator 1386, the forehead cushion support 1360 does not need a two-zone marking (such as that shown in FIG. 11-2).

3.2.8 Eighth Illustrated Embodiment

FIG. 11-15 illustrates an embodiment of a forehead support 1412 wherein the frame connector 1420 includes markings 1484 on the top thereof and the forehead cushion support 1460 includes a depth gauge or position indicator 1486 with a single marking 1487 that is movable relative to the markings 1484 on the frame connector 1420. As illustrated, the position indicator 1486 has a shroud-like configuration that encloses or covers the top of the frame connector 1420 and the marking 1487 is provided on a free end of the position indicator 1486. As the knob 1440 is rotated in use, the position indicator 1486 moves relative to the frame connector 1420 and the marking 1487 on the position indicator 1486 can be aligned with a selected one of the markings 1484 on the frame connector 1420 to indicate the forehead support's position.

In addition, the knob 1440 includes a raised portion or rib 1441 that provides grip for turning as well as tactile feedback of the knob's position.

The position indicator 1486 is sturdy and may assist in reducing and/or eliminating "rattle" between the forehead cushion support 1460 and the frame connector 1420. In addition, the position indicator 1486 makes the forehead cushion support 1460 less spindly and more integrated with the mask frame, e.g., especially in the fully extended position.

In an embodiment, the markings 1484, 1487 on the frame connector 1420 and the position indicator 1486 may be printed thereon, e.g., by pad printing, in any suitable color.

The raised portion 1441 and position indicator 1486 provide an arrangement that is relatively simple to align, assemble, and calibrate the adjustment starting point. Also, due to the position indicator 1486, the forehead cushion support 1460 does not need a two-zone marking (such as that shown in FIG. 11-2).

4. Alternative Embodiment of Adjustment Knob

FIGS. 12-1 to 12-8 illustrate an adjustment knob 1540 according to another embodiment of the present invention. The adjustment knob 1540 is similar to the adjustment knobs 40, 240 described above. In contrast, each prong or ratchet 1554 does not have a hinged or cantilevered configuration such as that of the prongs 54, 254 described above.

Specifically, each ratchet 1554 has a non-cantilever configuration wherein each end of the ratchet 1554 is supported by the segment 1548. The ratchet extends in the direction of rotation of the knob 1540, e.g. ratchet 1554 moved 90° with respect to prongs 54, 254. Thus, the profile of the ratchet bump 1556 extends substantially parallel to the mask frame at peak deflection, e.g., as the bump is deflected over the peaks of the ridges on the frame connector. This arrangement ensures a distributed load over the ratchet bump 1556, rather than a concentrated load applied to the supported end of a cantilever arrangement.

In an embodiment, the ratchet bump 1556 of each ratchet 1554 is angled at a with respect to a vertical axis, e.g., about 1 degree. This arrangement is more clearly shown in FIG. 12-7.

In an alternative embodiment, as shown in FIG. 13, a knob may include prongs 1654 with a hinged or cantilevered configuration wherein each prong 1654 has a trapezoid-like shape (rather than an hourglass shape such as that of the prong 54). This arrangement provides the prong 1654 with a relatively wide base at its proximal end to reduce stress. The ratchet bump 1656 is provided on the distal or free end of the prong 1654. The remaining elements of the knob may be substantially similar to the knob 40 described above.

5. Alternative Embodiment of Adjustment Knob and Frame Connector

FIGS. 14-1 to 15-4 illustrate an adjustment knob 1740 and a frame 1714 including a frame connector 1720 for a forehead support according to another embodiment of the present invention. The adjustment knob 1740 and frame connector 1720 may be used with a forehead cushion support such as that shown in FIGS. 5-1 to 5-7 for example.

Figures 11, 12, 13, 14, 15:
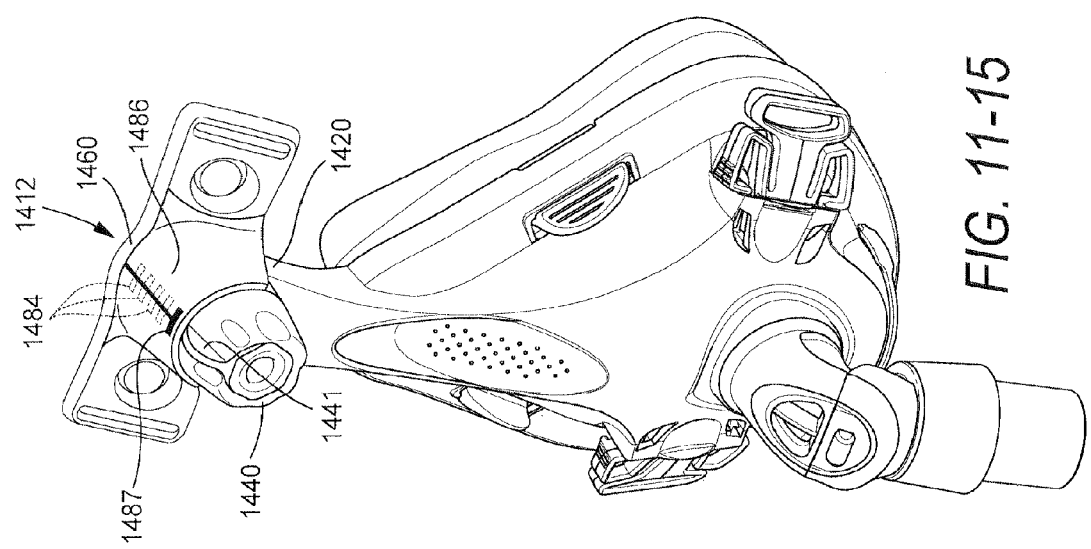
Figures 11, 12, 13, 14:
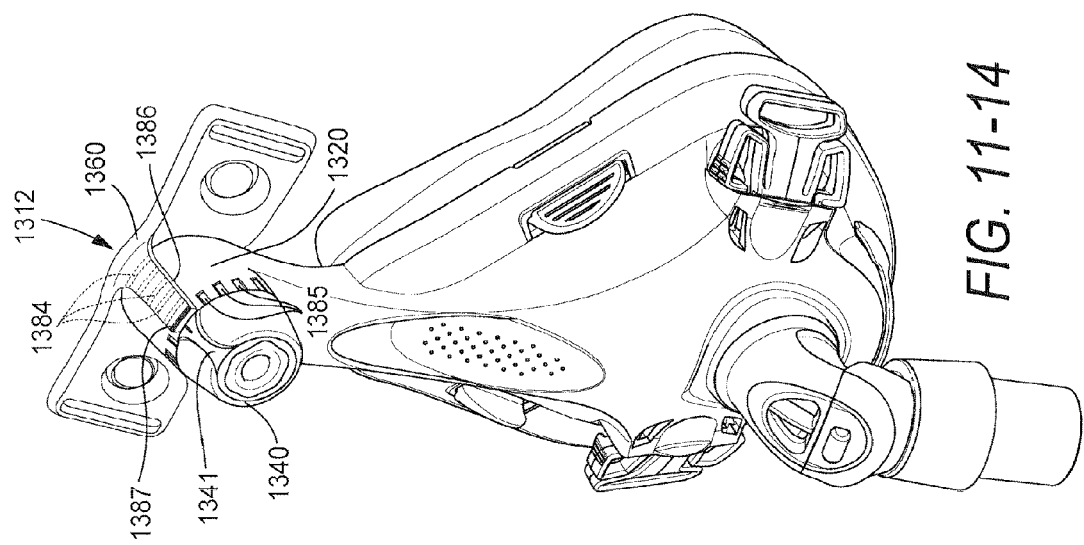

As shown in FIGS. 14-1 to 14-8, the adjustment knob 1740 is similar to the adjustment knob 40 described above. In contrast, the wall thickness of the segment 1748 defining resilient arms 1752 inserted into the frame connector 1720 has been increased, e.g., to about 1.85 mm. The arms 1752 are thicker to substantially avoid the arms 1752 flexing too easily and thus differentiate between the force required to adjust the knob 1740 and the force required to disassemble the knob 1740 from the frame connector 1720.

The annular rim 1750 provided on the segment 1748 still engages with retention features 1724 provided in the frame connector 1720 with a snap-fit. Since the segment 1748 is thicker, an annular recess 1751 is provided within which the retention features 1724 sit.

In addition, as best shown in FIGS. 14-5 and 14-6, each opening 1755 between the arms 1752 (in which respective resilient prongs 1754 are located) has a generally triangular shape. In the adjustment knob 40 described above, this opening has a generally T-shape. The knob 1740 functions the same as the knob 40. However, the triangular geometry of the opening 1755 may be beneficial for ratchet forces to the frame 1714 in use.

As shown in FIGS. 15-1 to 15-4, the frame 1714 and frame connector 1720 thereof is similar to the frame 14 and frame connector 20 described above. In contrast, the retention features 1724 on the frame connector 1720 have been increased in number to four retention features 1724 (rather than two retention features 24 in frame connector 20). The retention features 1724 are preferably equally spaced around the frame connector 1720 to prevent twisting of the adjustment knob 1740 on assembly and disassembly.

6. Alternative Embodiments of Forehead Cushion Support

FIGS. 16-1 to 19-7 illustrate four alternative embodiments of the forehead cushion support shown in FIGS. 8-1 to 8-7 described above. Each embodiment has a different design of deflection in order to allow insertion of the tube into the frame connector.

6.1 First Illustrated Alternative Embodiment

Figures 5, 16:
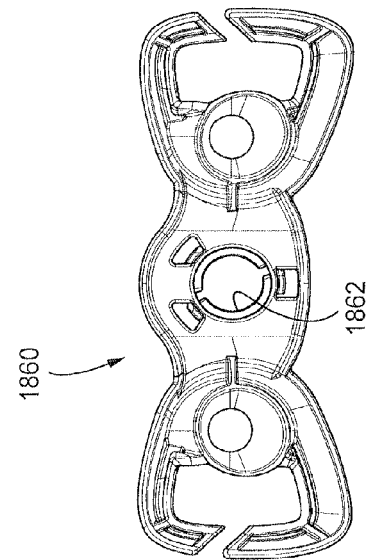
Figures 7, 16:
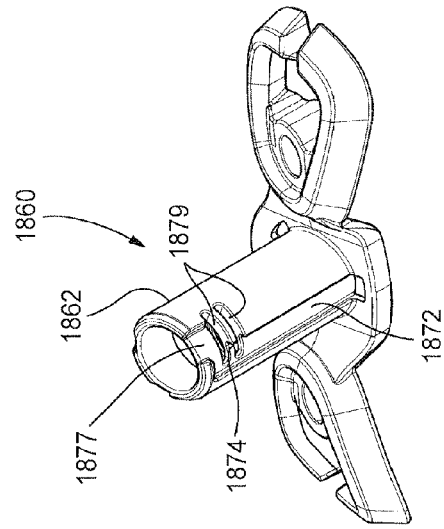
Figures 4, 16:
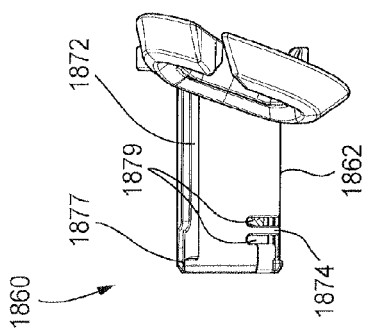
Figures 6, 16:
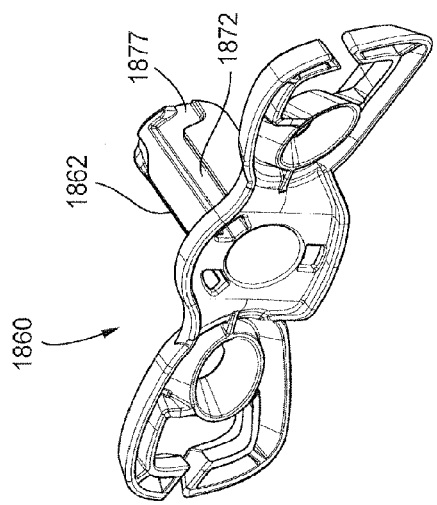

FIGS. 16-1 to 16-7 illustrate a forehead cushion support 1860 according to another embodiment of the present invention. The forehead cushion support 1860 is similar to the forehead cushion support 260 described above in FIGS. 8-1 to 8-7. In contrast, the tube 1862 includes key ways or elongated slots 1872 (e.g., three keyways) with a bayonet style configuration to allow insertion of the tube 1862 into the frame connector.

Specifically, an L-shaped or bayonet style slot 1877 is provided as a lead-in to each key way 1872. During assembly, the forehead cushion support 1860 must be twisted to guide the protrusions on the frame connector through respective L-shaped slots 1877 and into the respective key ways 1872.

In addition, at least one of the key ways 1872 includes a deflectable retention member 1874 adjacent the L-shaped slot 1877 to prevent inadvertent disassembly of the forehead cushion support 1860 from the frame connector. As illustrated, a slot 1879 is provided on each side of the retention member 1874 that allows the retention member 1874 to deflect on assembly of the tube 1862 to the frame connector.

6.2 Second Illustrated Alternative Embodiment

Figures 4, 17:
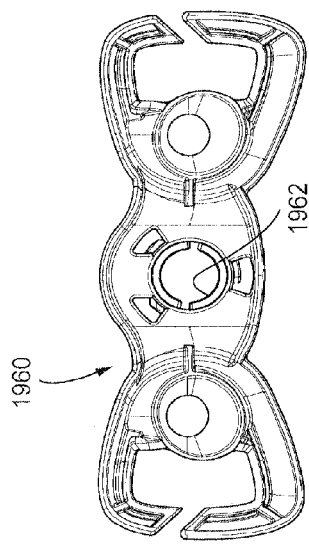
Figures 5, 17:
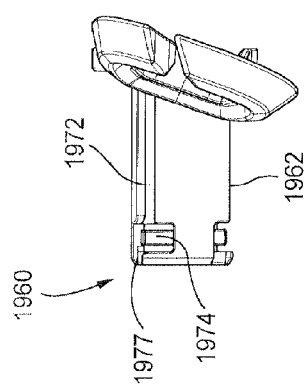
Figures 6, 17:
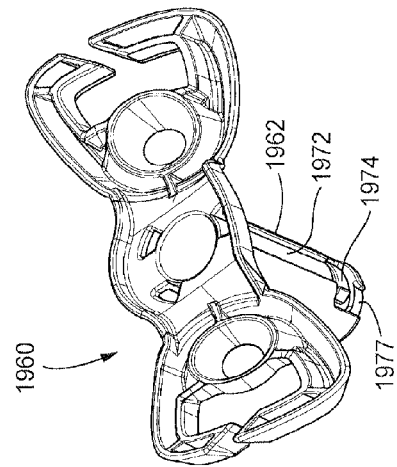
Figures 7, 17:
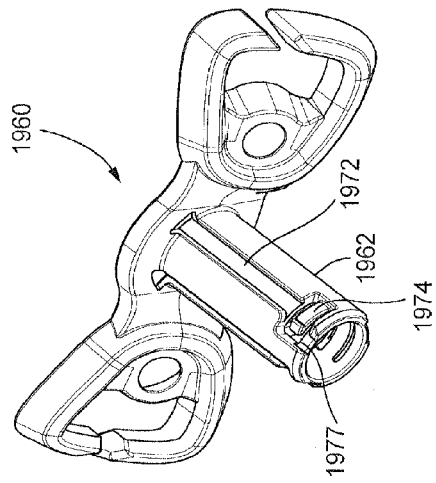

FIGS. 17-1 to 17-7 illustrate a forehead cushion support 1960 according to another embodiment of the present invention. The forehead cushion support 1960 is similar to the forehead cushion support 260 described above in FIGS. 8-1 to 8-7. In contrast, the tube 1962 includes key ways or elongated slots 1972 (e.g., three keyways) with a bayonet style configuration to allow insertion of the tube 1962 into the frame connector.

Specifically, an L-shaped or bayonet style slot 1977 is provided as a lead-in to each key way 1972. During assembly, the forehead cushion support 1960 must be twisted to guide the protrusions on the frame connector through respective L-shaped slots 1977 and into the respective key ways 1972.

In addition, at least one of the key ways 1972 includes a deflectable retention arm 1974, e.g., cantilevered arm, within the L-shaped slot 1977 to prevent inadvertent disassembly of the forehead cushion support 1960 from the frame connector. As illustrated, the retention arm 1974 is deflectable towards the center of the tube 1962 on assembly of the tube 1962 to the frame connector.

6.3 Third Illustrated Alternative Embodiment

Figures 5, 18:
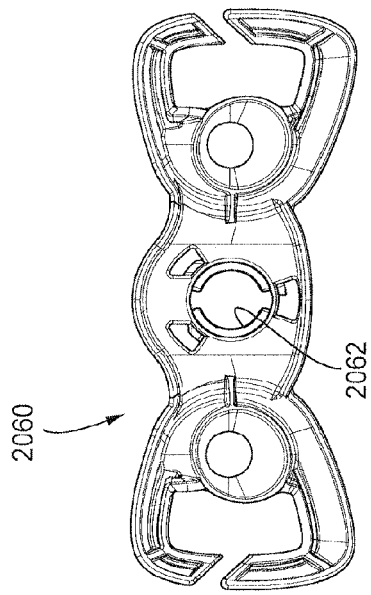
Figures 7, 18:
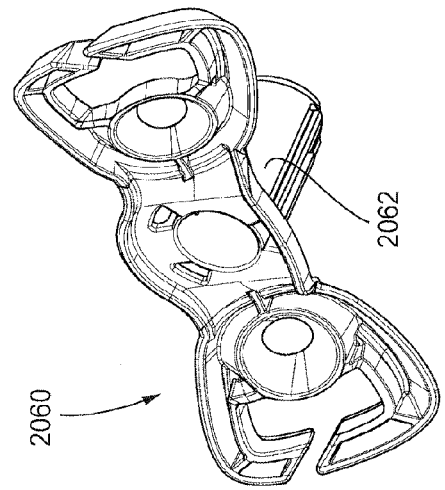
Figures 4, 18:
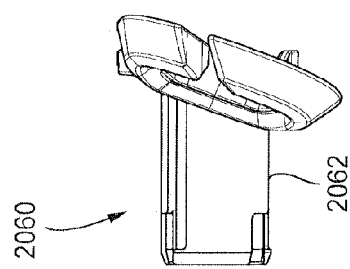
Figures 6, 18:
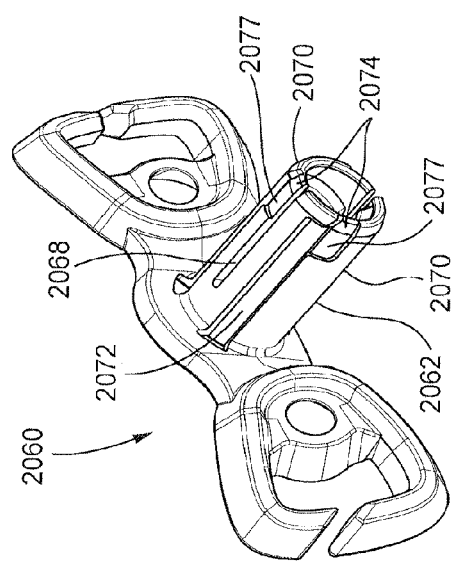

FIGS. 18-1 to 18-7 illustrate a forehead cushion support 2060 according to another embodiment of the present invention. The forehead cushion support 2060 is similar to the forehead cushion support 260 described above in FIGS. 8-1 to 8-7. In contrast, the tube 2062 includes two vertical splits 2068 (rather than horizontal splits 268 of tube 262) that divide the tube 2062 into two resilient arms 2070 which can deflect to allow insertion of the tube 2062 into the frame connector. The splits 2068 may have any suitable length along the tube 2062.

In addition, the tube 2062 includes key ways or elongated slots 2072 (e.g., three keyways) with a bayonet style configuration to allow insertion of the tube 2062 into the frame connector. Specifically, an L-shaped or bayonet style slot 2077 is provided as a lead-in to each key way 2072. During assembly, the forehead cushion support 2060 must be twisted to guide the protrusions on the frame connector through respective L-shaped slots 2077 and into the respective key ways 2072.

A ridge or retention bump 2074 is provided at the end of each L-shaped slot 2077. The ridges 2074 force the arms 2070 to deflect on assembly to the frame connector to prevent inadvertent disassembly of the forehead cushion support 2060 from the frame connector.

6.4 Fourth Illustrated Alternative Embodiment

Figures 5, 19:
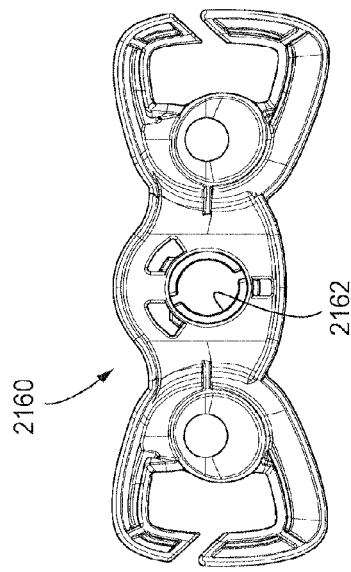
Figures 4, 19:
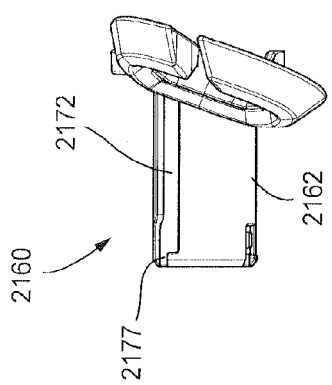
Figures 7, 19:
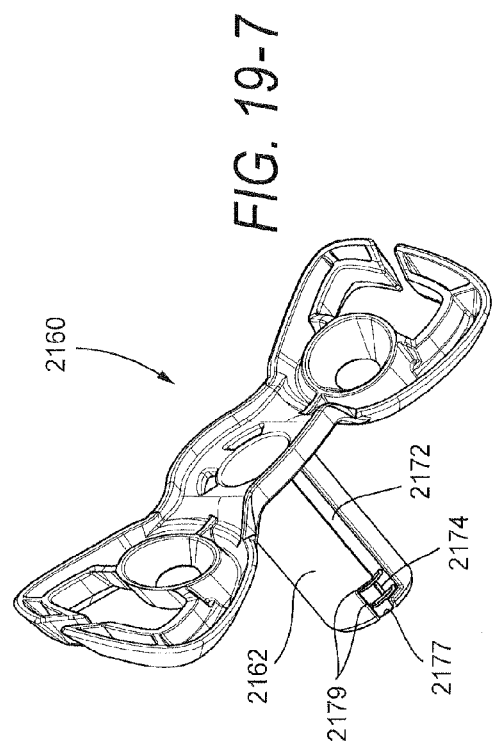
Figures 6, 19:
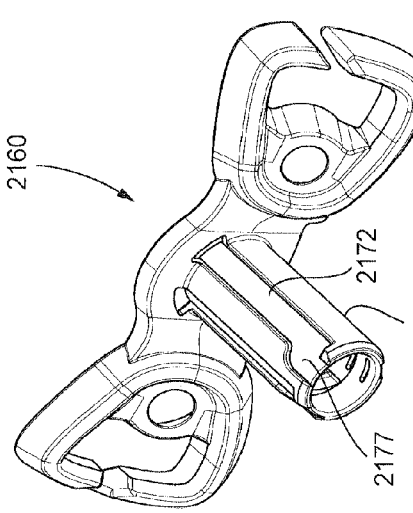

FIGS. 19-1 to 19-7 illustrate a forehead cushion support 2160 according to another embodiment of the present invention. The forehead cushion support 2160 is similar to the forehead cushion support 260 described above in FIGS. 8-1 to 8-7. In contrast, the tube 2162 includes key ways or elongated slots 2172 (e.g., three keyways) with a bayonet style configuration to allow insertion of the tube 2162 into the frame connector.

Specifically, an L-shaped or bayonet style slot 2177 is provided as a lead-in to each key way 2172. During assembly, the forehead cushion support 2160 must be twisted to guide the protrusions on the frame connector through respective L-shaped slots 2177 and into the respective key ways 2172.

In addition, at least one of the key ways 2172 includes a deflectable retention member 2174 within the L-shaped slot 2177 to prevent inadvertent disassembly of the forehead cushion support 2160 from the frame connector. As illustrated, a slot 2179 is provided on each side of the retention member 2174 that allows the retention member 2174 to deflect on assembly of the tube 2162 to the frame connector.

7. Curved Forehead Cushion Support

In an alternative embodiment, the tube of the forehead cushion support may be slightly curved so that the forehead cushion support moves along a curved or arcuate path.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike.

What is claimed is:
1. A forehead support for a mask assembly, the forehead support comprising:
   a frame connector;
   a forehead cushion support comprising a forehead cushion support plate and a tube, said forehead cushion support being linearly adjustable with respect to the frame connector along a longitudinal axis of the tube between a retracted position and an extended position;

a forehead cushion provided to the forehead cushion support plate;

at least two protrusions and at least two corresponding keyways positioned superior to a horizontal plane containing the longitudinal axis of the tube, the at least two protrusions and the at least two corresponding keyways structured to prevent rotation of the forehead cushion support about the longitudinal axis of the tube with respect to the frame connector, each of the at least two protrusions extending into a respective one of the at least two corresponding keyways; and a finger operable member projecting from the frame connector and movably mounted to the frame connector to allow adjustment of the forehead cushion support with respect to the frame connector.

2. A forehead support according to claim 1, wherein spaced position markings are provided on the tube.

3. A forehead support according to claim 2, wherein the spaced position markings are intervally numbered markings such that each intervally numbered marking is adjacent to an unnumbered marking on at least one side of each intervally numbered marking.

4. A forehead support according to claim 1, wherein the frame connector comprises an outer housing and an inner housing, the inner housing suspended internally from the outer housing to receive the tube and define a linear adjustment path of the forehead cushion support.

5. A forehead support according to claim 4, wherein a ridge is provided at a distal end of the tube to prevent separation of the frame connector and the forehead cushion support by engagement between the inner housing and the ridge in the extended position.

6. A forehead support according to claim 5, wherein the ridge, the tube, and the forehead cushion support plate comprise one piece.

7. A forehead support according to claim 1, wherein a ridge is provided at a distal end of the tube to prevent inadvertent disassembly of the forehead cushion support from the frame connector, the ridge shaped as a sloped projection.

8. A mask assembly for supplying breathable gas to a patient at positive pressure, the mask assembly comprising:
a mask frame;
a cushion provided to the mask frame, said cushion adapted to form a seal with the patient's face;
an elbow assembly provided to the mask frame, said elbow assembly adapted to be connected to an air delivery tube; and
a forehead support according to claim 1.

9. A forehead support according to claim 1, wherein spaced position markings are provided on the tube, the spaced position markings being intervally numbered markings such that each intervally numbered marking is adjacent to an unnumbered marking on at least one side of each intervally numbered marking,
wherein the frame connector comprises an outer housing and an inner housing, the inner housing suspended internally from the outer housing to receive the tube and define a linear adjustment path of the forehead cushion support, and
wherein a ridge is provided at a distal end of the tube to prevent separation of the frame connector and the forehead cushion support by engagement between the inner housing and the ridge in the extended position, the ridge being shaped as a sloped projection, and
wherein the ridge, the tube, and the forehead cushion support plate comprise one piece.

10. A forehead support for a mask assembly, the forehead support comprising:
a frame connector;
a forehead cushion support comprising a forehead cushion support plate and a tube, said forehead cushion support being linearly adjustable with respect to the frame connector along a longitudinal axis of the tube between a retracted position and an extended position;
a forehead cushion provided to the forehead cushion support plate;
a first protrusion and a corresponding first keyway, the first protrusion projecting into the corresponding first keyway; and
a second protrusion and a corresponding second keyway, the second protrusion projecting into the corresponding second keyway,
wherein the first protrusion, the corresponding first keyway, the second protrusion, and the corresponding second keyway are arranged to prevent incorrect assembly of the forehead cushion support to the frame connector,
wherein the forehead cushion support plate is angled with respect to a plane perpendicular to the longitudinal axis of the tube,
wherein position markings are provided on the tube, and
wherein the first protrusion, the corresponding first keyway, the second protrusion, and the corresponding second keyway, and the position markings are positioned superior to a horizontal plane containing the longitudinal axis of the tube.

11. A forehead support according to claim 10, further comprising a third protrusion and a corresponding third keyway.

12. A forehead support according to claim 10, wherein the position markings comprise spaced position markings.

13. A forehead support according to claim 12, wherein the spaced position markings are intervally numbered markings such that each intervally numbered marking is adjacent to an unnumbered marking on at least one side of each intervally numbered marking.

14. A forehead support according to claim 10, wherein the frame connector comprises an outer housing and an inner housing, the inner housing spaced internally within the outer housing to define a linear adjustment path of the forehead cushion support relative to the frame connector by engagement of the inner housing with an outer surface of the tube.

15. A forehead support according to claim 14, wherein a ridge is provided at a distal end of the tube to prevent separation of the frame connector and the forehead cushion support plate by engagement of the ridge to the inner housing in the extended position, and
wherein the ridge, the tube, and the forehead cushion support plate comprise one piece.

16. A mask assembly for supplying breathable gas to a patient at positive pressure, the mask assembly comprising:
a mask frame;
a cushion provided to the mask frame, said cushion adapted to form a seal with the patient's face;
an elbow assembly provided to the mask frame, said elbow assembly adapted to be connected to an air delivery tube; and
a forehead support according to claim 10.

17. A forehead support according to claim 10, wherein the position markings comprise spaced position markings, the spaced position markings being intervally numbered markings such that each intervally numbered marking is adjacent to an unnumbered marking on at least one side of each intervally numbered marking, wherein the frame connector comprises an outer housing and an inner housing, the inner housing spaced internally within the outer housing to define a linear adjustment path of the forehead cushion support relative to the frame connector by engagement of the inner housing with an outer surface of the tube, wherein a ridge is provided at a distal end of the tube to prevent separation of the frame connector and the forehead cushion support plate by engagement of the ridge to the inner housing in the extended position, and wherein the ridge, the tube, and the forehead cushion support plate comprise one piece.

18. A forehead support for a mask assembly, the forehead support comprising:
- a frame connector;
- a forehead cushion support comprising a forehead cushion support plate and a tube, said forehead cushion support being linearly adjustable with respect to the frame connector along a longitudinal axis of the tube between a retracted position and an extended position;
- a forehead cushion provided to the forehead cushion support plate;
- a first keyway and protrusion set and a second keyway and protrusion set arranged asymmetrically about the tube to prevent misassembly of the forehead support to the frame connector, each protrusion configured to extend into a respective keyway; and
- a projection provided to the frame connector and configured to allow adjustment of the forehead cushion support relative to the frame connector, wherein the forehead cushion support plate is positioned at an angle with respect to a plane perpendicular to the longitudinal axis of the tube, and wherein numbered position markings are provided on the tube.

19. A forehead support according to claim 18, further comprising a third keyway and protrusion set.

20. A forehead support according to claim 18, wherein the numbered position markings comprise spaced, numbered position markings.

21. A forehead support according to claim 20, wherein the spaced, numbered position markings are intervally numbered markings such that each intervally numbered marking is adjacent to an unnumbered marking on at least one side of each intervally numbered marking.

22. A forehead support according to claim 18, wherein the frame connector comprises an outer housing and an inner housing, the inner housing spaced internally within the outer housing to define a linear adjustment path of the forehead cushion support along the inner housing.

23. A forehead support according to claim 22, wherein a ridge is provided at a distal end of the tube to prevent separation of the frame connector and the forehead cushion support plate by engagement between the inner housing and the ridge in the extended position.

24. A forehead support according to claim 23, wherein the ridge, the tube, and the forehead cushion support plate comprise one piece.

25. A forehead support according to claim 18, wherein a ridge projects from the tube opposite the forehead cushion support plate to prevent inadvertent disassembly of the frame connector and the forehead cushion support.

26. A mask assembly for supplying breathable gas to a patient at positive pressure, the mask assembly comprising:
- a mask frame;
- a cushion provided to the mask frame, said cushion adapted to form a seal with the patient's face;
- an elbow assembly provided to the mask frame, said elbow assembly adapted to be connected to an air delivery tube; and
- a forehead support according to claim 18, wherein the first keyway and protrusion set and the second keyway and protrusion set are arranged asymmetrically relative to a horizontal plane containing the longitudinal axis of the tube.

27. A forehead support according to claim 18, wherein the numbered position markings comprise spaced, numbered position markings, the spaced, numbered position markings being intervally numbered markings such that each intervally numbered marking is adjacent to an unnumbered marking on at least one side of each intervally numbered marking, wherein the frame connector comprises an outer housing and an inner housing, the inner housing spaced internally within the outer housing to define a linear adjustment path of the forehead cushion support along the inner housing, and wherein a ridge is provided at a distal end of the tube to prevent separation of the frame connector and the forehead cushion support plate by engagement between the inner housing and the ridge in the extended position, the ridge, the tube, and the forehead cushion support plate comprising one piece.

28. A forehead support according to claim 18, wherein said projection comprises an adjustment knob movably mounted to the frame connector and threadably engaged with the forehead cushion support such that turning movement of the adjustment knob causes the forehead cushion support to be moved between the retracted position and the extended position, wherein the adjustment knob includes two external ridges that are diametrically opposed to one another, wherein the adjustment knob includes a resilient prong having a bump to selectively engage a series of ridges provided to the frame connector to provide indexed incremental adjustment, wherein the adjustment knob includes a threaded shaft having a two-start design to engage with an internal thread of the tube of the forehead cushion support, wherein the adjustment knob includes a plurality of horns on an annular surface to act as a smooth bearing surface, wherein the adjustment knob further comprises an annular rim to engage with a retention feature provided in the frame connector; and wherein the frame connector includes a retention feature to engage with the annular rim of the adjustment knob.

* * * * *